United States Patent
Riley et al.

(10) Patent No.: US 9,464,311 B2
(45) Date of Patent: Oct. 11, 2016

(54) METHOD FOR IDENTIFYING MODULATORS OF UBIQUITIN LIGASES

(71) Applicant: E3X BIO, Menlo Park, CA (US)

(72) Inventors: Brigit Riley, Mill Valley, CA (US); Jennifer Johnston, Mill Valley, CA (US); David Morgans, Los Altos, CA (US)

(73) Assignee: E3X Bio, Inc., Menlo Park, CA (US)

( * ) Notice: Subject to any disclaimer, the term of this patent is extended or adjusted under 35 U.S.C. 154(b) by 0 days.

(21) Appl. No.: 14/268,977

(22) Filed: May 2, 2014

(65) Prior Publication Data

US 2014/0327158 A1     Nov. 6, 2014

Related U.S. Application Data

(60) Provisional application No. 61/818,796, filed on May 2, 2013, provisional application No. 61/932,139, filed on Jan. 27, 2014.

(51) Int. Cl.
    *C12Q 1/37*     (2006.01)
    *C12Q 1/25*     (2006.01)

(52) U.S. Cl.
    CPC .......... *C12Q 1/25* (2013.01); *G01N 2333/9015* (2013.01); *G01N 2500/02* (2013.01)

(58) Field of Classification Search
    CPC ................................................. C07K 2319/95
    USPC .......................................................... 530/350
    See application file for complete search history.

(56) References Cited

U.S. PATENT DOCUMENTS

| 9,079,966 B2 * | 7/2015 | Brik ...................... C07K 14/00 |
| 2006/0211747 A1 | 9/2006 | Furet et al. |
| 2008/0248458 A1 | 10/2008 | Cao et al. |
| 2010/0021941 A1 | 1/2010 | Marblestone et al. |

FOREIGN PATENT DOCUMENTS

WO    WO 2011/098998 A2    8/2011

OTHER PUBLICATIONS

Love et al.: "*Ubiquitin C-terminal electrophiies are activity-based probes for identification and mechanistic study of ubiquitin conjugating machinery*,"; ACS Chem Biol., Apr. 17, 2009, vol. 4, pp. 275-287.
Van Wijk et al.: "*The family of ubiquitin-conjugating enzymes (E2s): deciding between life and death of proteins*,"; FASEB J., Nov. 25, 2009, vol. 24, pp. 981-993.
Zhang at al.: "*The inflammation-associated Salmonella SopA is a HECT-like E3 ubiquitin ligase*"; Mol Microbiol, Nov. 1, 2006, vol. 62, pp. 786-793.
Chen et al.: "*Genetic and expression aberrations of E3 ubiquitin ligases in human breast cancer*"; Mol Cancer Res., Oct. 1, 2006, vol. 4, pp. 695-707.
International Search Report regarding PCT/US2014/036678.

* cited by examiner

*Primary Examiner* — Maryam Monshipouri
(74) *Attorney, Agent, or Firm* — DLA Piper LLP (US)

(57) ABSTRACT

The present invention provides a screen which exploits mechanism-based activity probes that specifically and covalently modify the active site cysteine thiol residue of E3 Ub ligases including, but not limited to the HECT and RBR family. The activity probes are used to screen for activators and inhibitors of E3 Ub ligases, and to interrogate the functional state of E3 Ub ligases in human disease.

10 Claims, 15 Drawing Sheets

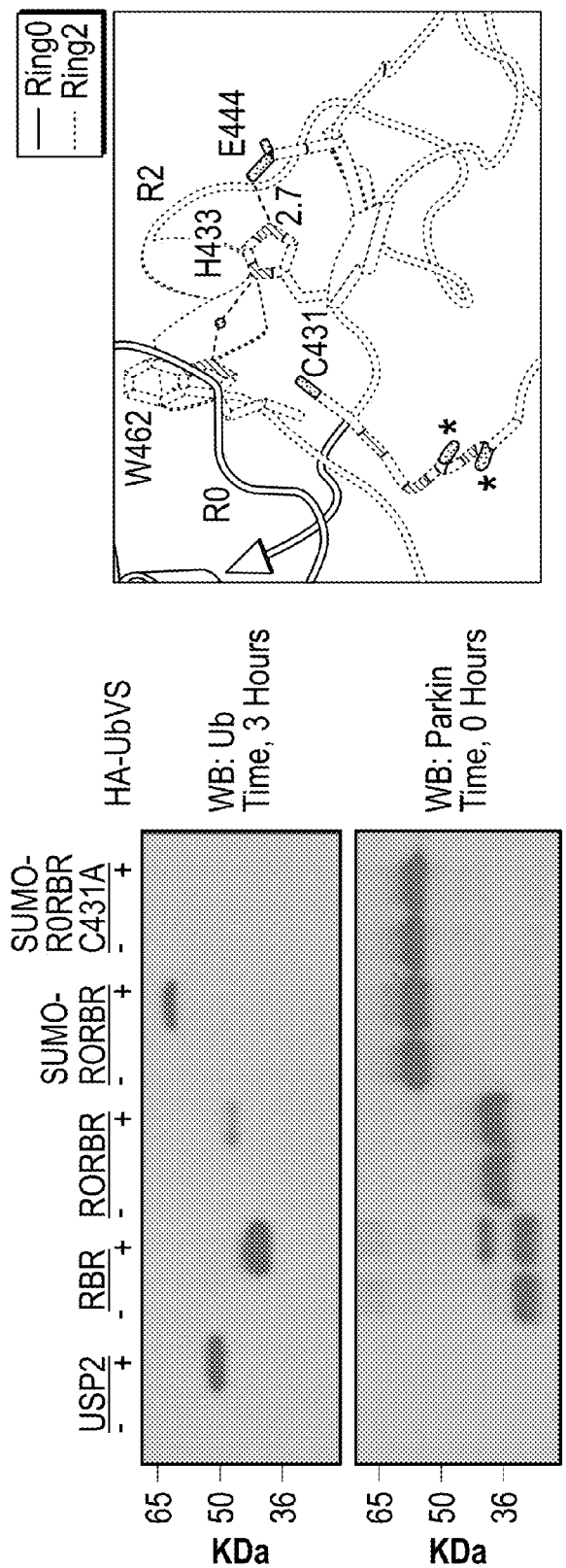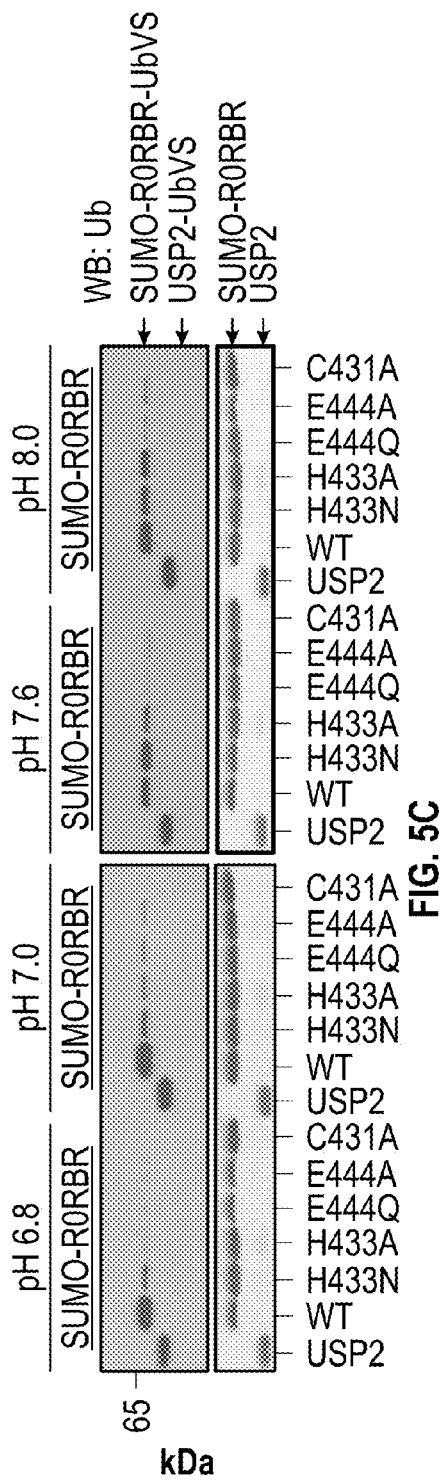
FIG. 5A
FIG. 5B
FIG. 5C

Acrylates

Vinyl Sulfonyls

Acyloxymethylketones

Beta-Lactones

Cyanamides

Epoxysuccinates

SEQUENCE LISTING

```
<160> NUMBER OF SEQ ID NOS: 8

<210> SEQ ID NO 1
<211> LENGTH: 15
<212> TYPE: PRT
<213> ORGANISM: Artificial Sequence
<220> FEATURE:
<223> OTHER INFORMATION: Synthetic construct

<400> SEQUENCE: 1

Cys Leu Pro Val Ile Ser Ala Glu Asn Trp Lys Pro Ala Thr Lys
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic construct

<400> SEQUENCE: 2

Leu Pro Val Ile Ser Ala Glu Asn Trp Lys Pro Ala Thr Lys
1               5                   10
```

```
<210> SEQ ID NO 3
<211> LENGTH: 15
<212> TYPE: PRT
<213> ORGANISM: Artificial Sequence
<220> FEATURE:
<223> OTHER INFORMATION: Synthetic construct

<400> SEQUENCE: 3

Lys Thr Ala Pro Lys Trp Asn Glu Ala Ser Ile Val Pro Leu Cys
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Synthetic construct

<400> SEQUENCE: 4

Lys Thr Ala Pro Lys Trp Asn Glu Ala Ser Ile Val Pro Leu
1               5                   10

<210> SEQ ID NO 5
<211> LENGTH: 26
<212> TYPE: PRT
<213> ORGANISM: Artificial Sequence
<220> FEATURE:
<223> OTHER INFORMATION: Synthetic construct

<400> SEQUENCE: 5

Tyr Pro Phe Lys Pro Pro Lys Ile Thr Phe Lys Thr Lys Ile Tyr His
1               5                   10                  15

Pro Asn Ile Asp Glu Lys Gly Gln Val Cys
            20                  25

<210> SEQ ID NO 6
<211> LENGTH: 16
<212> TYPE: PRT
<213> ORGANISM: Artificial Sequence
<220> FEATURE:
<223> OTHER INFORMATION: Synthetic construct

<400> SEQUENCE: 6

Ile Gln Lys Glu Ser Thr Leu His Leu Val Leu Arg Leu Arg Gly Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic construct

<400> SEQUENCE: 7

Ile Gln Lys Glu Ser Thr Leu His Leu Val Leu Arg Leu Arg Gly
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic construct

<400> SEQUENCE: 8
```

```
Gly Gly Arg Leu Arg Leu Val Leu His Leu Thr Ser Glu Lys Gly Ile
1               5                   10                  15
```

METHOD FOR IDENTIFYING MODULATORS OF UBIQUITIN LIGASES

CROSS REFERENCE TO RELATED APPLICATIONS

This application claims the benefit of priority under §119(e) of U.S. Ser. No. 61/932,139, filed Jan. 27, 2014 and U.S. Ser. No. 61/818,796 filed May 2, 2013. The disclosure of the prior application is considered part of and is incorporated by reference in its entirety in the disclosure of this application.

INCORPORATION OF SEQUENCE LISTING

The material in the accompanying Sequence Listing is hereby incorporated by reference into this application. The accompanying sequence listing text file, name E3X1100_3_Sequence_Listing_ST25, was created on May 2, 2014 and is 3 KB. The file can be assessed using Microsoft Word on a computer that uses Windows OS.

FIELD OF THE INVENTION

The present invention relates generally to modification of proteins and, more specifically, to methods for identifying compounds that modulate ubiquitin pathway enzymes.

BACKGROUND INFORMATION

Ubiquitin (Ub) is a 76 amino acid protein. Many biochemical pathways are regulated in part by post-translational modification of proteins with Ub and ubiquitin-like (UbL) molecules. This post-translational protein modification by Ub, a process known as ubiquitination or ubiquitylation, is involved in the regulation of biological processes such as protein degradation, gene transcription, cell-cycle progression, DNA repair, apoptosis, virus budding and receptor endocytosis. Precise regulation is achieved through the opposing actions of Ub/UbL-specific conjugating and deconjugating enzymes. Members of the Ub and UbL protein family include Ub, SUMO, NEDD8, ISG15, URM1, FAT10, UFM1, LC3, GATE-16, GABARAP and ATG12. These related proteins are structurally similar, and are activated, conjugated, and released from conjugates in a mechanism akin to that for Ub. There is cross-talk between conjugation pathways with some substrate proteins becoming targeted by more than one type of modifier. Ub is found only in eukaryotic organisms in which it shows strong sequence conservation.

Post-translational modification of proteins by Ub and UbLs regulates almost every aspect of biology and enables complex and reversible regulation of protein stability and activity. Because of this broad role in cell biology, dysfunction in Ub pathway enzymes results in a multitude of human diseases, and suggests there is a large population of enzymes that may be amenable to small molecule manipulation. Covalent attachment of Ub/UbLs to substrates is achieved through a canonical E1-E2-E3 enzyme cascade, whereby Ub is activated by E1 and transferred to an E2 via a high-energy thioester bond. E2 carrying activated Ub then binds to an E3 enzyme, where Ub transfer to a lysine residue on substrate is poised to occur. The mechanics of transfer from E3 to substrate depends on the specific class of E3 ligase involved. These ligases comprise over 500 different proteins and are categorized into multiple classes defined by the structural element of their E3 functional activity. The E3 ligases are grouped into two main classes: the HECT ligases containing an active site cysteine which serves to accept Ub prior to substrate transfer, and the RING E3 ligases, which contain zinc finger-like domains that act as scaffolds enabling transfer of Ub directly from an E2 enzyme to a substrate. The RBR (RING-between-RING) is a subclass of E3 Ub ligases that are considered RING/HECT hybrids in that similar to RING ligases coordinate zinc and bind E2, but also contain an active site cysteine similar to HECT ligases. Specifically, both HECT and RING ligases transfer an activated Ub from a thioester to the 8-amino acid group of a lysine residue on a substrate; however, HECT ligases have an active site cysteine that forms an intermediate thioester bond with Ub, while RING ligases function as a scaffold to allow direct Ub transfer from the E2 to substrate.

Parkin is a RBR E3 ligase that functions in the covalent attachment of ubiquitin to specific substrates, and mutations in Parkin are linked to Parkinson's disease, cancer and mycobacterium infection. The RBR family of E3 ligases are suggested to function with a canonical RING domain and a catalytic cysteine residue usually restricted to HECT E3 ligases, thus termed RING/HECT hybrid enzymes. Parkin has been proposed to function as a RBR ligase such that it encompasses both of the major classes of E3 ligase in one protein. Specifically, it may function with both a catalytic cysteine and a classical RING motif for binding E2. While recent work has established that Parkin has four RING domains, coordinating eight zinc (Zn) molecules, the exact residues coordinating these Zn atoms, and the organization of each of the RING domains with respect to each other are not known. Parkin has been described to have latent activity that can be activated with carbonyl cyanide 3-chlorphenyl-hydrazone (CCCP) in cells, although it is not completely known how the latent state becomes activated at the molecular level, and whether purified Parkin protein contains a similar latent state has not yet been established. Regulation of Parkin activity by phosphorylation has been described, but the subsequent molecular events post-phosphorylation are not understood. Finally, while catalytic networks have been investigated for E3 ligases it is not yet clear whether they function with a classic triad/dyad-based mechanism, or whether catalysis occurs through a hydrogen-bonding network. For deubiquitinating enzymes (DUBS) it has been demonstrated that the cleavage of Ub from a substrate occurs through a classic triad/dyad mechanism, utilizing a critical catalytic cysteine residue, and a histidine residue in close proximity.

The process by which Ub is added to a protein by an E3 Ub ligase is the reverse reaction of removing Ub executed by deubiqutinating enzymes (DUBs). A variety of Ub activity probes have been developed to monitor the removal of Ub by DUBs. As described herein, Ub activity probes can also be used to screen compounds screen to identify small molecules that activate or inhibit E3 Ub ligases.

SUMMARY OF THE INVENTION

The present invention provides a screen which exploits mechanism-based activity probes that specifically and covalently modify the active site cysteine thiol residue of E3 ubiquitin ligases including, but not limited to the HECT and RBR family. The activity probes are used to screen for modulators of E3 Ub ligases, and to interrogate the functional state of E3 Ub ligases in human disease.

In one embodiment, the present invention provides a method to identify a modulator of ubiquitin ligase activity comprising contacting a ubiquitin ligase with a compound;

contacting the mixture with an activity probe, wherein the activity probe comprises a label; measuring the probe label on the ligase, wherein an increase or decrease in probe label on the ligase as compared to a control identifies the compound as a modulator of ubiquitin ligase activity. In an aspect, the ligase is an E3 ligase. In a preferred aspect, the E3 ligase is a HECT or RBR family ligase. In another aspect, the compound is a small molecule. In an additional aspect, the activity probe comprises a ubiquitin conjugating peptide, a reactive chemical moiety, a ubiquitin peptide and a label. In a further aspect, the ubiquitin conjugating peptide is E2. In another aspect, the label is a fluorescent, enzymatic or radioactive label. In an aspect, the reactive chemical moiety can be acrylates, vinyl sulfonyls, acyloxymethylketones, beta-lactones, cyanamides or epoxysuccinates. In a further aspect, the activity probe further comprises an epitope tag. In one aspect, the decrease or increase in label is determined by a method known in the art which may be FRET, HTRF or ELISA. In an additional aspect, a decrease in probe label on the ligase is indicative of an inhibitor of the ligase and an increase in probe label on the ligase is indicative of an activator of the ligase.

In an additional embodiment, the invention provides a small molecule inhibitor or activator of ubiquitin ligase identified by contacting a ubiquitin ligase with a compound; contacting the mixture with an activity probe, wherein the activity probe comprises a label; measuring the probe label on the ligase, wherein an increase or decrease in probe label on the ligase as compared to a control identifies the compound as a modulator of ubiquitin ligase activity.

In a further embodiment, the invention provides an activity probe comprising a ubiquitin conjugating peptide, a reactive chemical moiety and a ubiquitin peptide. In one aspect, the activity probe further comprising a label and an epitope tag. In an aspect, the ubiquitin conjugating peptide is an E2 peptide. In a preferred aspect, the E2 peptide forms an E2-E3 interaction domain with an E3 ligase. In an additional aspect, the chemical moiety reacts with the active site cysteine of a ubiquitin ligase. In a further aspect, the chemical moiety can be acrylates, vinyl sulfonyls, acyloxymethylketones, beta-lactones, cyanamides, alpha amino nitriles or epoxysuccinates. In another aspect, the ubiquitin peptide contains a E3-ubiquitin interaction domain. In an aspect, the ubiquitin conjugating peptide is SEQ ID NO:1, SEQ ID NO:2, SEQ ID NO:3, SEQ ID NO:4 or SEQ ID NO:5. In another aspect, the ubiquitin peptide is SEQ ID NO:6, SEQ ID NO:7 or SEQ ID NO:8.

In another embodiment, the present invention provides a method of identifying a compound which inhibits a ubiquitin ligase from a pathogen comprising contacting the ubiquitin ligase with a compound; contacting the mixture with an activity probe, wherein the activity probe comprises a label and measuring the probe label on the ligase, wherein a decrease in probe label on the ligase as compared to a control identifies the compound as an inhibitor of ubiquitin ligase activity. In one aspect the ubiquitin ligase is SopA or the novel E3 ligase family (NEL). In an additional aspect, the pathogen is *Salmonella enterica, E. coli, Shigella* or *Pseudomonas*.

In one embodiment, the present invention provides a method of identifying a ubiquitin ligase with enhanced enzyme activity in tumors comprising contacting a tumor sample containing a ubiquitin ligase with an activity probe, wherein the activity probe comprises a label and measuring the probe label on the ligase, wherein an increase in probe label on the ligase as compared to a control identifies a ubiquitin ligase with enhanced enzyme activity. In one aspect, the tumor is lymphomas, CLL, small lymphocytic lymphoma, marginal cell B-Cell lymphoma, Burkett's Lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, or head and neck cancer.

BRIEF DESCRIPTION OF THE DRAWINGS

FIGS. 5*a-c* demonstrate the catalytic machinery of Parkin. A. The activity probe HA-UbVS was incubated with various Parkin constructs (or USP2 control) to determine intrinsic Parkin enzymatic activity. B. The potential catalytic triad residues C431, H433 and E444 are misaligned. H433 is engaged in a water-mediated hydrogen bond with W462 and is ~5.1 Å from C431. A GG-C431 motif is present, which Could serve as a classical oxyanion hole during catalysis. C. Parkin probe reactivity requires elements of a classical catalytic triad.

with two 180° views. One face of Parkin has a higher number of mutations than the other face. Several areas contain higher densities of mutations, and these regions are circled. These functional regions include the area near the R1:IBR interface, the putative E2 binding site, and the area around the catalytic C431

Figure 8A:
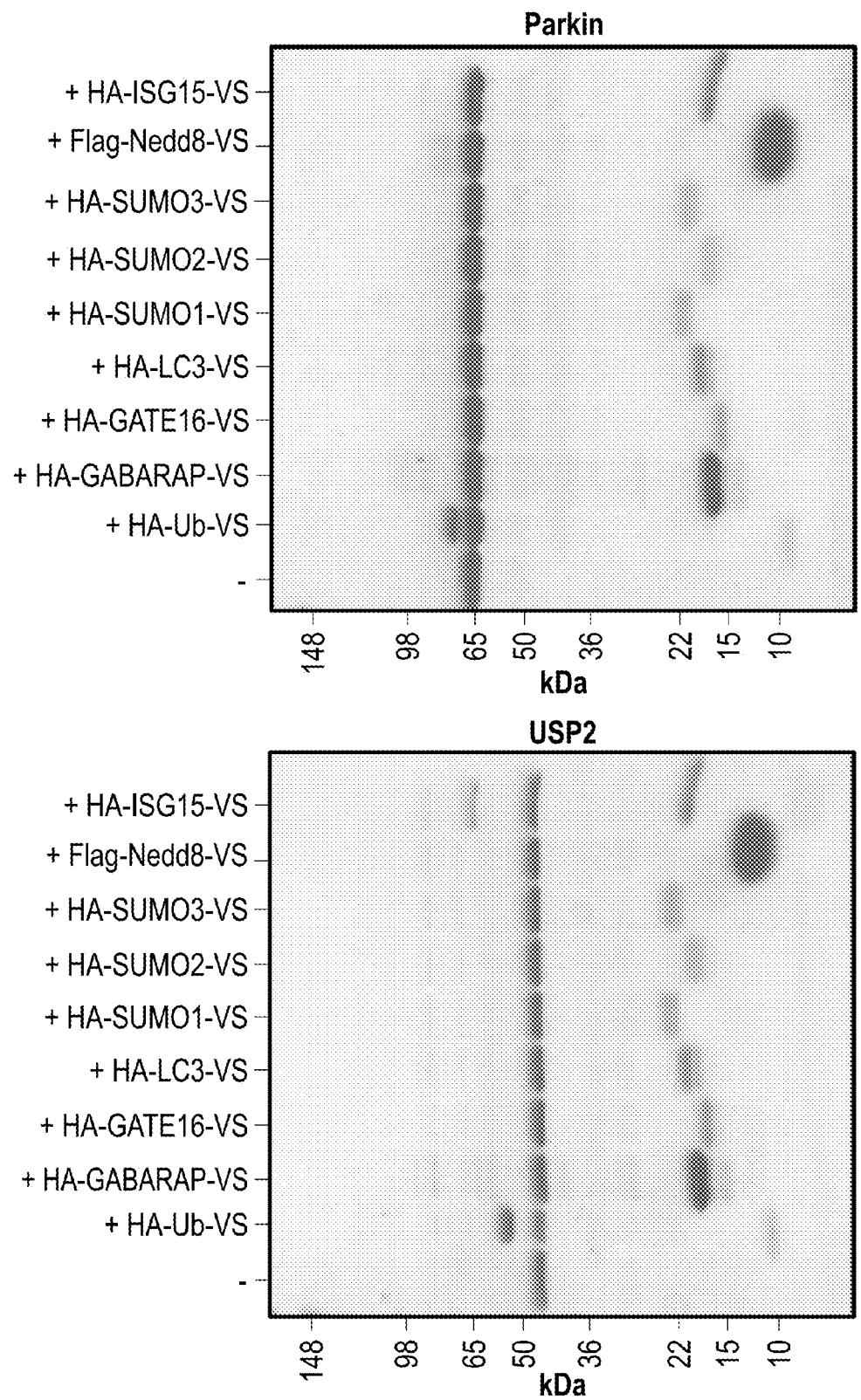
Figure 8B:
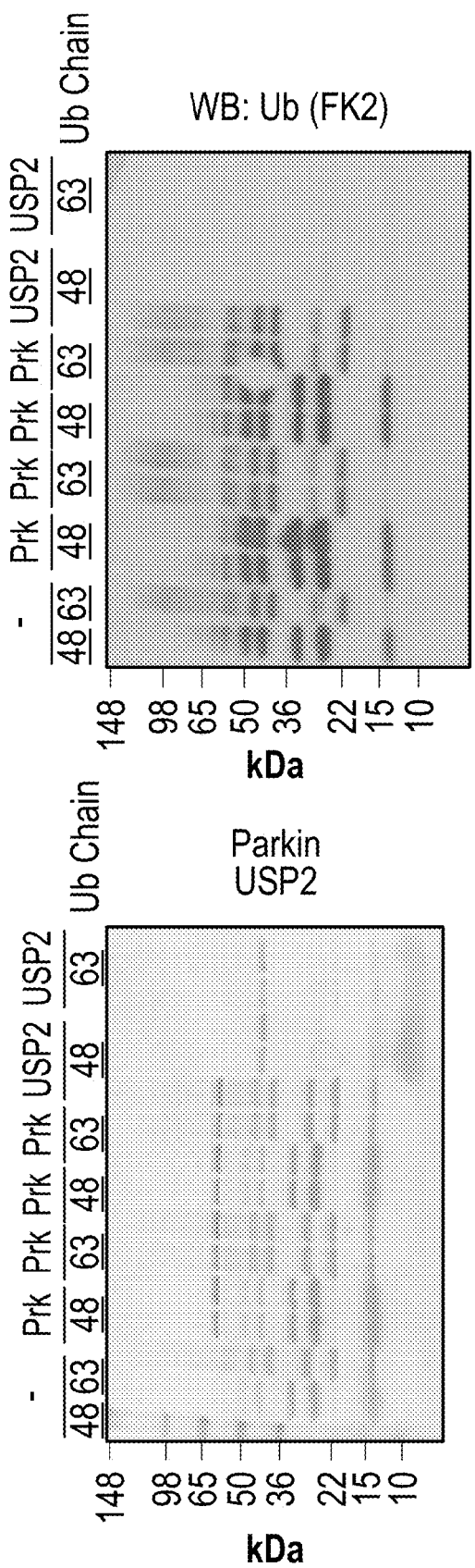

FIGS. 8a-b show Parkin reactivity with HA-Ub-VS is specific and Parkin is not a deubiquinating enzyme (DUB). A. The DUB USP2 reacts with HA-UbVS and HA-Isg15Vs and was used as a positive control. Parkin reacts specifically with HA-UbVS and to a weak extent NEDD8, and no reactivity with other UB-like VS probes. B. Parkin or USP2 were incubated with a pure UbK48 (2-7) or (UbK63) (2-7) chains.

FIGS. 9a-f depict the generic structures of reactive chemical moieties.

DETAILED DESCRIPTION OF THE INVENTION

The present invention provides a screen which exploits mechanism-based activity probes that specifically and covalently modify the active site cysteine thiol residue of E3 Ub ligases including, but not limited to the HECT and RBR family. The activity probes are used to screen for activators and inhibitors of E3 Ub ligases, and to interrogate the functional state of E3 Ub ligases in human disease.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Ubiquitination is a post-translational modification where ubiquitin is attached to a substrate protein. The addition of ubiquitin can affect proteins in many ways: It can signal for their degradation via the proteasome, alter their cellular location, affect their activity, and promote or prevent protein interactions. Ubiquitination is carried out in three main steps: activation, conjugation, and ligation, performed by ubiquitin-activating enzymes (E1s), ubiquitin-conjugating enzymes (E2s), and ubiquitin ligases (E3s), respectively. The result of this sequential cascade binds ubiquitin to lysine residues on the protein substrate via an isopeptide bond or to the amino group of the protein's N-terminus via a peptide bond.

Ubiquitin-activating enzymes, also known as E1 enzymes, catalyze the first step in the ubiquitination reaction, which (among other things) can target a protein for degradation via a proteasome. This covalent attachment of ubiquitin or ubiquitin-like proteins to targeted proteins is a major mechanism for regulating protein function in eukaryotic organisms. Ubiquitin-activating enzyme (E1) starts the ubiquitination process. The E1 enzyme along with ATP binds to the ubiquitin protein. The E1 enzyme then passes the ubiquitin protein to a second protein, called Ubiquitin carrier or conjugation protein (E2). The E2 protein complexes with an Ubiquitin protein ligase (E3). This Ubiquitin protein ligase recognizes which protein needs to be tagged and catalyzes the transfer of ubiquitin to that protein. This pathway repeats itself until the target protein has a full chain of ubiquitin attached to itself.

Ubiquitin-conjugating enzymes, also known as E2 enzymes and more rarely as ubiquitin-carrier enzymes, perform the second step in the ubiquitination reaction that targets a protein for degradation via the proteasome. The ubiquitination process covalently attaches ubiquitin, a short protein of 76 amino acids, to a lysine residue on the target protein. Once a protein has been tagged with one ubiquitin molecule, additional rounds of ubiquitination form a polyubiquitin chain that is recognized by the proteasome's 19S regulatory particle, triggering the ATP-dependent unfolding of the target protein that allows passage into the proteasome's 20S core particle, where proteases degrade the target into short peptide fragments for recycling by the cell.

A ubiquitin ligase (also called an E3 ubiquitin ligase) is a ligase enzyme that combines with a ubiquitin-containing E2 ubiquitin-conjugating enzyme, recognizes the target protein that is to be ubiquinated, and causes the attachment of ubiquitin to a lysine on the target protein via an isopeptide bond. An E3 ubiquitin ligase targets specific protein substrates for degradation by the proteasome. In general, the ubiquitin ligase is involved in poly-ubiquitination: a second ubiquitin is attached to the first, a third is attached to the second, and so forth. Poly-ubiquitination marks proteins for degradation by the proteasome. Each contains particular protein domains capable of binding the E2 conjugase, as well as a substrate-specific domain for binding the target. Many E2- and substrate-binding domains exist. This wide variety has been discovered to fall into specific groups called ubiquitin-ligase families including a RING (Really Interesting New Gene) domain binds the E2 conjugase and might be found to mediate enzymatic activity in the E2-E3 complex and a HECT domain, which is involved in the transfer of ubiquitin from the E2 to the substrate. In molecular biology, a RING finger domain is a protein structural domain of zinc finger type which contains a Cys3HisCys4 amino acid motif which binds two zinc cations. This protein domain contains from 40 to 60 amino acids. Many proteins containing a RING finger play a key role in the ubiquitination pathway. The HECT domain is a protein domain found in ubiquitin-protein ligases. Proteins containing this domain at the C terminus include ubiquitin-protein ligase, which regulates ubiquitination of CDC25. Ubiquitin-protein ligase accepts ubiquitin from an E2 ubiquitin-conjugating enzyme in the form of a thioester, and then directly transfers the ubiquitin to targeted substrates. A cysteine residue is required for ubiquitin-thiolester formation.

Examples of E3 ligases include E3A, mdm2, Anaphase-promoting complex (APC), UBR5 (EDD1), SOCS/BC-box/eloBC/CUL5/RING, LNXp80, CBX4, CBLL1, HACE1, HECTD1, HECTD2, HECTD3, HECW1, HECW2, HERC1, HERC2, HERC3, HERC4, HUWE1, ITCH, NEDD4, NEDD4L, Parkin, PPIL, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE4A, UBE4B, UBOX5, UBR5, WWP1 and WWP2.

The process by which Ub is added to a protein by an E3 Ub ligase is the reverse reaction of removing Ub executed by deubiqutinating enzymes (DUBs). A variety of Ub activity probes have been developed to monitor the removal of Ub by DUBs. The Ub activity probes consist of an Ub moiety with an epitope tag at the N-terminus, and a modified C-terminus, such that following the terminal glycine-glycine (GlyGly) there is a reactive chemical moiety, such as an electrophilic trap (e.g. vinyl sulfone (VS)). The reactive chemical moiety irreversibly reacts with the active site cysteine in the E3 Ub ligase. The use of Ub activity probe is a basis for a compound screen to identify small molecules that activate or inhibit E3 Ub ligases. It was found that the degree of reactivity of E3 Ub ligases with the Ub activity probe correlates directly with the degree of auto-ubiquitination activity of E3 Ub ligase.

Figure 1:
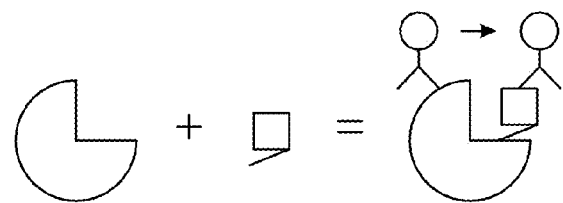
FIG. 1 is a depiction of the method for identifying a ubiquitin ligase modulator wherein E3 ligase protein is incubated with small molecules after which an activity probe is added and the level of probe label is measured.

To screen for small molecules that modulate ubiquitin ligases a screen was developed to identify small molecules that modulate E3 Ub ligases by increasing or decreasing auto-inhibition. Specifically, E3 Ub ligases are incubated with test compounds, followed by the addition of an activity probe. Increased probe label indicates the compounds have increased the accessibility of activity probe to E3 Ub ligase and indicates that the compound is an activator of E3 Ub ligase. A decrease in probe label will indicate the compound has effectively blocked accessibility of probe to the active site, presumably by binding tightly to the active site cysteine in the active site, or by altering the ligase to the point where the probe can no longer react, thereby indicating that the compound is an inhibitor of E3 ligase. The readout for activity will be through one of the following assays TR-FRET/HTRF/AlphaScreen/AlphaLISA, all of which have a similar principle which is using the epitope tag on the activity probe (or an antibody to Ub itself) and an antibody for the E3 Ub ligase to monitor the amount of activity probe covalently attached to the E3 Ub ligase (FIG. 1).

In one embodiment, the present invention provides a method to identify a modulator of ubiquitin ligase activity comprising contacting a ubiquitin ligase with a compound; contacting the mixture with an activity probe, wherein the activity probe comprises a label; measuring the probe label on the ligase, wherein an increase or decrease in probe label on the ligase as compared to a control identifies the compound as a modulator of ubiquitin ligase activity. In an aspect, the ligase is an E3 ligase. In a preferred aspect, the E3 ligase is a HECT or RBR family ligase. In another aspect, the compound is a small molecule. In an additional aspect, the activity probe comprises a ubiquitin conjugating peptide, a reactive chemical moiety, a ubiquitin peptide and a label. In a further aspect, the ubiquitin conjugating peptide is E2. In another aspect, the label is a fluorescent, enzymatic or radioactive label. In an aspect, the reactive chemical moiety is acrylates, vinyl sulfonyls, acyloxymethylketones, beta-lactones, cyanamides or epoxysuccinates. In a further aspect, the activity probe further comprises an epitope tag. In one aspect, the decrease or increase in label is determined by a method known in the art which may be FRET, HTRF or ELISA. In an additional aspect, a decrease in probe label on the ligase is indicative of an inhibitor of the ligase and an increase in probe label on the ligase is indicative of an activator of the ligase.

In an additional embodiment, the invention provides a small molecule inhibitor or activator of ubiquitin ligase identified by contacting a ubiquitin ligase with a compound; contacting the mixture with an activity probe, wherein the activity probe comprises a label; measuring the probe label on the ligase, wherein an increase or decrease in probe label on the ligase as compared to a control identifies the compound as a modulator of ubiquitin ligase activity.

As used herein, a "modulator" is any compound or molecule that increases or decrease ubiquitin ligase activity. A modulator can be a chemical compound such as a small molecule or a biologic molecule.

As used herein, an "activity probe" is a probe that is used to measure ubiquitin ligase activity. The probe consists of three main elements:
  1. an ubiquitin-conjugating enzyme peptide, specifically an E2 peptide that forms the E2-E3 interaction domain;
  2. a reactive chemical moiety designed to react with the active site cysteine of the E3 ligase; and
  3. a ubiquitin peptide; specifically a Ub peptide that forms the c-terminus of Ub and extends towards the N-terminus a sufficient distance to contain the E3-Ub interaction domain.

These three elements are arranged 1-2-3 such that the reactive chemical moiety is in between the E2 peptide and the Ub peptide. An activity probe can further comprise a label and an epitope tag. Examples of labels and epitope tags include a His tag and an HA antibody (see Example 1).

As used herein, a "reactive chemical moiety" is a moiety which reacts with a ubiquitin ligase. The reactive chemical moiety reacts strongly or irreversibly with the active site of the ubiquitin ligase. Specifically, the reactive chemical moiety reacts with a cysteine residue in the active site of E3 ligase. Examples of reactive chemical moieties include acrylates, vinyl sulfonayls, acyloxymethylketones, beta-lactones, cyanamides, alpha amino nitriles and epoxysuccinates.

Figure 9A:
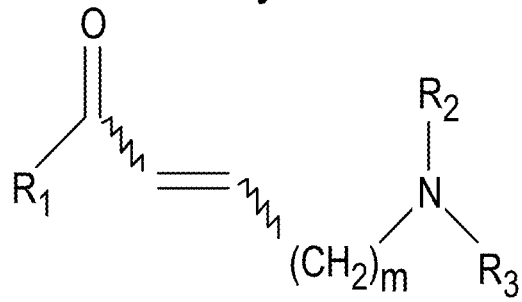

In specific examples, for the acrylates of the instant invention wherein R1 is attached to SEQ ID NO:1, SEQ ID NO:2, SEQ ID NO:3, SEQ ID NO:4 or SEQ ID NO:5 through a chemically stable, small alkyl linker to cysteine residue of amino acid sequence, directly to serine or another natural or unnatural amino acid bearing OH or $NH_2$ in the side chain, directly or through a small, chemically stable small alkyl linker to another side chain OH or $NH_2$ of a natural or unnatural amino acid in a sequence similar to SEQ ID NO:1, SEQ ID NO:2, SEQ ID NO:3, SEQ ID NO:4 or SEQ ID NO:5 where up to 5 residues may be other naturally occurring amino acids; wherein m=1-6 and may be part of an aromatic, heteroaromatic, carbocyclic or heterocyclic ring; wherein R2 is H or Methyl; wherein R3 is attached directly or through a small, chemically stable small alkyl linker to the C-terminus of a sequence of SEQ ID NO: 6, SEQ ID NO:7 or SEQ ID NO:8 or shorter where up to 5 residues may be other naturally occurring amino acids (FIG. 9a).

Figure 9B:
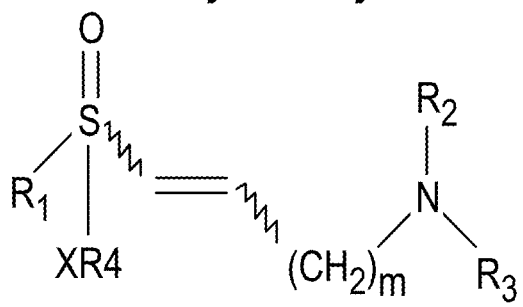

In specific examples, for the vinyl sulfonayls of the instant invention wherein R1 is attached to SEQ ID NO:1, SEQ ID NO:2, SEQ ID NO:3, SEQ ID NO:4 or SEQ ID NO:5 through a chemically stable, small alkyl linker to cysteine residue of amino acid sequence, directly to serine or another natural or unnatural amino acid bearing OH or $NH_2$ in the side chain, directly or through a small, chemically stable small alkyl linker to another side chain OH or $NH_2$ of a natural or unnatural amino acid in a sequence similar to SEQ ID NO:1, SEQ ID NO:2, SEQ ID NO:3, SEQ ID NO:4 or SEQ ID NO:5 where up to 5 residues may be other naturally occurring amino acids; wherein m=1-6 and may be part of an aromatic, heteroaromatic, carbocyclic or heterocyclic ring; wherein R2 is H or Methyl; wherein R3 is attached directly or through a small, chemically stable small alkyl linker to the C-terminus of a sequence of SEQ ID NO: 6, SEQ ID NO:7 or SEQ ID NO:8 or shorter where up to 5 residues may be other naturally occurring amino acids; wherein X is O or N; and wherein R4 is absent where X is O and Methyl where X is N (FIG. 9b).

Figure 9C:
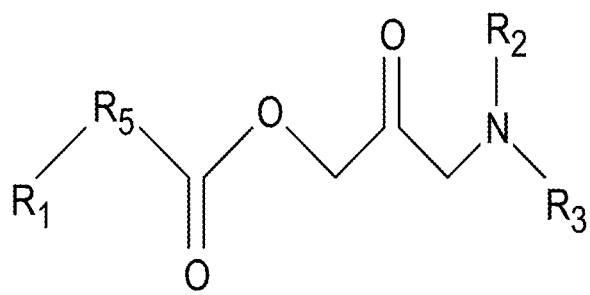

In specific examples, for the aclyoxymethylketones of the instant invention wherein R1 is attached to SEQ ID NO:1, SEQ ID NO:2, SEQ ID NO:3, SEQ ID NO:4 or SEQ ID NO:5 through a chemically stable, small alkyl linker to cysteine residue of amino acid sequence, directly to serine or another natural or unnatural amino acid bearing OH or $NH_2$ in the side chain, directly or through a small, chemically stable small alkyl linker to another side chain OH or $NH_2$ of a natural or unnatural amino acid in a sequence similar to SEQ ID NO:1, SEQ ID NO:2, SEQ ID NO:3, SEQ ID NO:4 or SEQ ID NO:5 where up to 5 residues may be other naturally occurring amino acids; wherein m=1-6 and may be part of an aromatic, heteroaromatic, carbocyclic or heterocyclic ring; wherein R2 is H or Methyl; wherein R3 is attached directly or through a small, chemically stable small alkyl linker to the C-terminus of a sequence of SEQ ID NO: 6, SEQ ID NO:7 or SEQ ID NO:8 or shorter where up to 5 residues may be other naturally occurring amino acids; wherein X is O or N; wherein R4 is absent for where X is O and Methyl where X is N; and wherein R5 is an aromatic ring, suitably substituted to allow attachment to R1 and facilitate the ability of R1-R5-COO to act as leaving a group when interacting with the E3 active site cysteine (FIG. 9c).

Figure 9D:
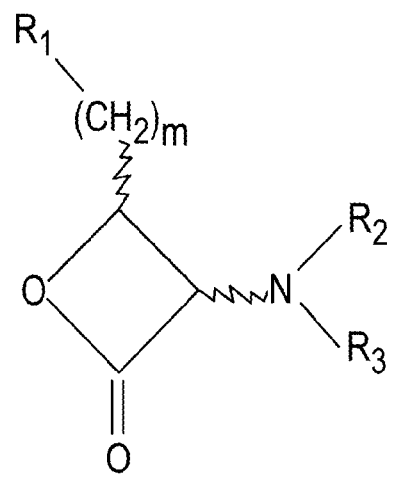

In specific examples, for the beta-lactones of the instant invention wherein R1 is attached to SEQ ID NO:1, SEQ ID NO:2, SEQ ID NO:3, SEQ ID NO:4 or SEQ ID NO:5 through a chemically stable, small alkyl linker to cysteine residue of amino acid sequence, directly to serine or another natural or unnatural amino acid bearing OH or $NH_2$ in the side chain, directly or through a small, chemically stable small alkyl linker to another side chain OH or $NH_2$ of a natural or unnatural amino acid in a sequence similar to SEQ ID NO:1, SEQ ID NO:2, SEQ ID NO:3, SEQ ID NO:4 or SEQ ID NO:5 where up to 5 residues may be other naturally occurring amino acids; wherein m=1-6 and may be part of an aromatic, heteroaromatic, carbocyclic or heterocyclic ring; wherein R2 is H or Methyl; wherein R3 is attached directly or through a small, chemically stable small alkyl linker to the C-terminus of a sequence of SEQ ID NO: 6, SEQ ID NO:7 or SEQ ID NO:8 or shorter where up to 5 residues may be other naturally occurring amino acids (FIG. 9d).

Figure 9E:
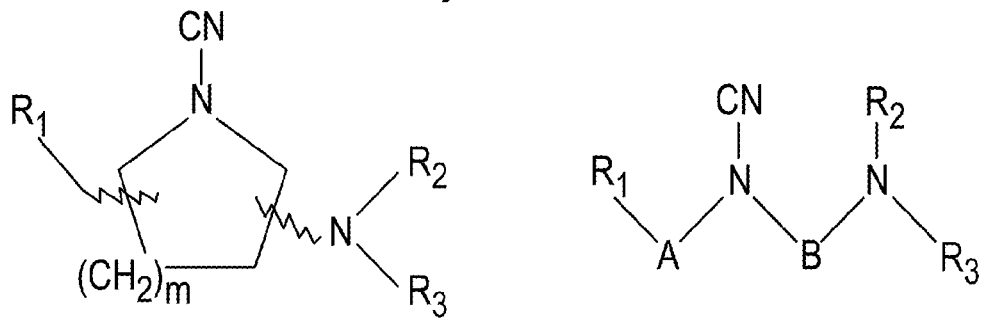

In specific examples, for the cyanamides of the instant invention wherein R1 is attached to SEQ ID NO:1, SEQ ID NO:2, SEQ ID NO:3, SEQ ID NO:4 or SEQ ID NO:5 through a chemically stable, small alkyl linker to cysteine residue of amino acid sequence, directly to serine or another natural or unnatural amino acid bearing OH or $NH_2$ in the side chain, directly or through a small, chemically stable small alkyl linker to another side chain OH or $NH_2$ of a natural or unnatural amino acid in a sequence similar to SEQ ID NO:1, SEQ ID NO:2, SEQ ID NO:3, SEQ ID NO:4 or SEQ ID NO:5 where up to 5 residues may be other naturally occurring amino acids or wherein R1 is absent; wherein m=1-6 and may be part of an aromatic, heteroaromatic, carbocyclic or heterocyclic ring; wherein R2 is H or Methyl; wherein R3 is attached directly or through a small, chemically stable small alkyl linker to the C-terminus of a sequence of SEQ ID NO: 6, SEQ ID NO:7 or SEQ ID NO:8 or shorter where up to 5 residues may be other naturally occurring amino acids; wherein X is O or N; wherein R4 is absent for where X is O and Methyl where X is N; and wherein R5 is an aromatic ring, suitably substituted to allow attachment to R1 as described above and facilitate the ability of R1-R5-COO to act as leaving a group when interacting with the E3 active site cysteine. Generically, NR2R3 may not be attached to the heterocyclic ring adjacent to ring nitrogen. A may be 1-3 optionally substitute carbons and may be part of a ring, B may be 2-3 optionally substituted carbons and may be part of a ring (FIG. 9e).

Figure 9F:
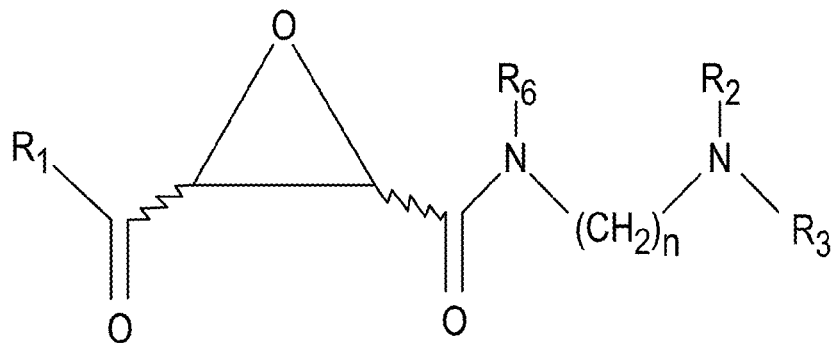

In specific examples, for the epoxysuccinates of the instant invention wherein R1 is attached to SEQ ID NO:1, SEQ ID NO:2, SEQ ID NO:3, SEQ ID NO:4 or SEQ ID NO:5 through a chemically stable, small alkyl linker to cysteine residue of amino acid sequence, directly to serine or another natural or unnatural amino acid bearing OH or $NH_2$ in the side chain, directly or through a small, chemically stable small alkyl linker to another side chain OH or $NH_2$ of a natural or unnatural amino acid in a sequence similar to SEQ ID NO:1, SEQ ID NO:2, SEQ ID NO:3, SEQ ID NO:4 or SEQ ID NO:5 where up to 5 residues may be other naturally occurring amino acids; wherein m=1-6 and may be part of an aromatic, heteroaromatic, carbocyclic or heterocyclic ring; wherein R2 is H or Methyl; wherein R3 is attached directly or through a small, chemically stable small alkyl linker to the C-terminus of a sequence of SEQ ID NO: 6, SEQ ID NO:7 or SEQ ID NO:8 or shorter where up to 5 residues may be other naturally occurring amino acids, wherein N=2-5 and may be part of a ring and wherein R6 is H or a methyl group (FIG. 9f).

The activity probes of the present invention can be used for the identification of small molecules that inhibit pathogen effector E3 Ub ligases that contain an active site cysteine. Effectors from pathogens mimic mammalian E3 Ub ligases for their own benefit, and although the overall sequence homology to mammalian E3 Ub ligases is divergent, the sequences around the active site cysteine are conserved. In most cases the substrates of these effector ligases are unknown, but overexpression of catalytically dead ligases prevents infection suggesting that the activity of E3 Ub ligases is essential to pathogenesis. Examples include SopA from *Salmonella enterica* and the novel E3 ligase family (NEL) from *E. coli, Shigella* and *Pseudomonas*. Using activity probes as a functional readout of enzyme activity of these effector ligases we aim to identify small molecules that specifically inhibit the effector E3 Ub ligase activity.

The activity probes of the present invention can also be used for the identification of E3 Ub ligases that are activated in tumors. Transcriptional profiling of human cancers has been widely used to identify causative genes whose levels are different between normal and diseased tissue. However, there are limitations to this approach for the study of enzymes because transcript abundance does not always correlate with activity; thus, there is a real need for accurate quantitative measurements that report on enzyme activity. Tagged activity probes and mass spectrometry can be used to identify E3 Ub ligases with significantly enhanced enzyme activity in tumors.

E3 Ub ligases are important cell regulators for many areas of biology, and as such the molecules we identify can be used across many indications, including, but not restricted to, metabolic disorders, neurodegeneration, inflammation, infection, cancer.

In another embodiment, the present invention provides a method of identifying a compound which inhibits a ubiquitin ligase from a pathogen comprising contacting the ubiquitin ligase with a compound; contacting the mixture with an activity probe, wherein the activity probe comprises a label and measuring the probe label on the ligase, wherein a decrease in probe label on the ligase as compared to a control identifies the compound as an inhibitor of ubiquitin ligase activity. In one aspect the ubiquitin ligase is SopA or the novel E3 ligase family (NEL). In an additional aspect, the pathogen is *Salmonella enterica, E. coli, Shigella* or *Pseudomonas*.

In one embodiment, the present invention provides a method of identifying a ubiquitin ligase with enhanced enzyme activity in tumors comprising contacting a tumor sample containing a ubiquitin ligase with an activity probe, wherein the activity probe comprises a label and measuring probe label on the ligase, wherein an increase in probe label on the ligase as compared to a control identifies a ubiquitin ligase with enhanced enzyme activity. In one aspect, the tumor is lymphomas, CLL, small lymphocytic lymphoma, marginal cell B-Cell lymphoma, Burkett's Lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, or head and neck cancer.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Assay to Identify Modulators of Ubiquitin Ligase Activity

To identify modulators of ubiquitin ligase, E3 Ub ligase is diluted in assay buffer (50 mM HEPES, 50 mM NaCl, 0.01% NP40, pH 6.8) and added to wells of a multi-well non-binding plate. Compounds are added to each well followed by at least 30-minute incubation. An activity probe (such as Ub-vinyl sulfone (Ub-VS)) is added and the reaction allowed to proceed at room temperature. Antibody to the epitope tag of the E3 Ub ligase (for example His) conjugated with donor such as Europium (III) cryptate or nickel chelate acceptor beads is added to the wells. Antibody to the epitope tag (for example HA) of Ub-VS conjugated with acceptor such as XL665, or Biotinylated Ub antibody (conjugated with streptavidin donor beads) will be added to the wells in stop buffer and the mixture incubated for a to be determined optimized period of time.

Light emission was read using a plate reader. The amount of light emission is proportional to the amount of active E3 that reacted with activity probe. In the presence of E3 Ub ligase conjugated to probe, the two beads come into close proximity to each other. The excitation of donor beads results in the liberation of singlet oxygen molecules that triggers energy transfer in the acceptor bead, resulting in light emission. Light emission can be measured by any means known in the art including FRET, HTRF and ELISA. Where there was a decrease in probe label, the compound inhibited ubiquitin ligase. Where there was an increase in probe label, the compound activated ubiquitin ligase.

Example 2

Determination of Structure and Catalytic Activity of an E3 Ligase

Parkin is an example of an E3 ligase. A 1.58 Å structure of Parkin R0RBR is presented, that reveals fold architecture for the four RING domains, and several unpredicted interfaces. Examination of the Parkin active site suggests a catalytic network consisting of C431 and H433. In cells, mutation of C431 eliminates Parkin-catalyzed degradation of mitochondria, and capture of an ubiquitin oxyester confirms C431 as Parkin's cellular active site. Our data confirm that Parkin is a RING/HECT hybrid, and is the first crystal structure of a RBR E3 ligase at atomic resolution, providing insight into this disease-related protein. To gain insight into the domain organization of Parkin, and regulation of Parkin ligase activity, it was sought to obtain the crystal structure of Parkin at high resolution. This 1.58 Å structure reveals that Parkin forms a relatively compact overall structure with multiple unpredicted domain interfaces. These interfaces form the basis for understanding a latent and activated state for Parkin, as well as provide insight into the role of the active site cysteine, C431, and the network of residues in proximity to C431 that facilitate catalysis.

Figure 3A:
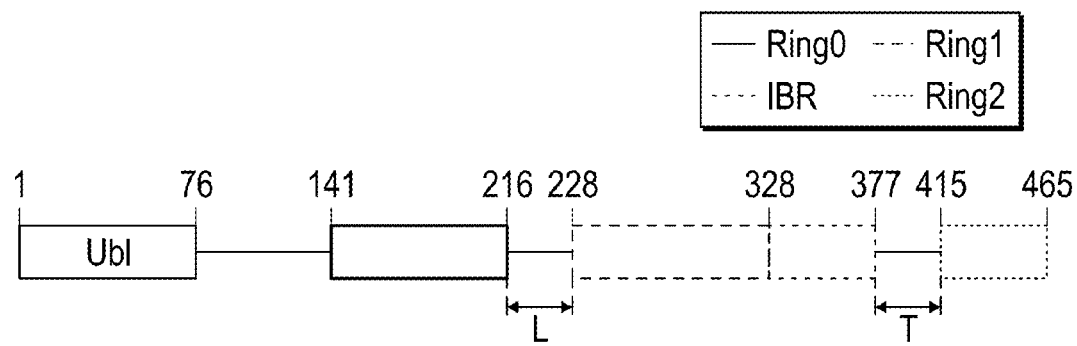
FIGS. 3*a-c* show overall Parkin domain organization and RING structures. A. Schematic diagram of Parkin indicating linear domain organization and structural domain boundaries. L denotes linker and T, the tether. B. Overall ribbon diagram of R0RBR (left) and overall surface structure (right). C. View of individual RING domains.

To gain insight into the RBR class of E3 ligase, crystals of Parkin R0RBR (residues 141-465) that includes RING (R0) and the RBR domains (FIGS. 3a and 3b) were grown. The structure was determined by analysis of multiwavelength anomalous diffraction (MAD) data using the signal from Zn ions bound by the individual RING domains and was refined against high resolution data to 1.58 A (Coordinates and structure factors have been deposited in the RCSB protein data bank under accession codes 4I1F (Parkin R0RBR-P223) and 4I1H (Parkin R0RBR-S223)). Two structures of Parkin were solved to determine if there were any notable structural differences between the sequence of Parkin originally reported (containing P223) and the updated sequence (S223). Overall the two structures were extremely similar; however, the loop containing S223 was visible in Parkin-R0RBR but not in the P223 structure. Each RING domain binds two Zn ions and resolves discrepancies in the literature regarding Zn coordination (FIG. 3c). The R0 domain (residues 141-216) is a previously unobserved domain fold (based on Dali) while R1 (residues 228-328) shows the classical cross-brace arrangement and Zn coordination of canonical RING domains. The IBR domain is similar to the published NMR structure. The R2 domain of Parkin most closely resembles IBR domains, and is very similar to HOIP IBR domain. Conversely, R2 differs significantly from the closely related HHAR1 R2 NMR structure.

Figure 2:
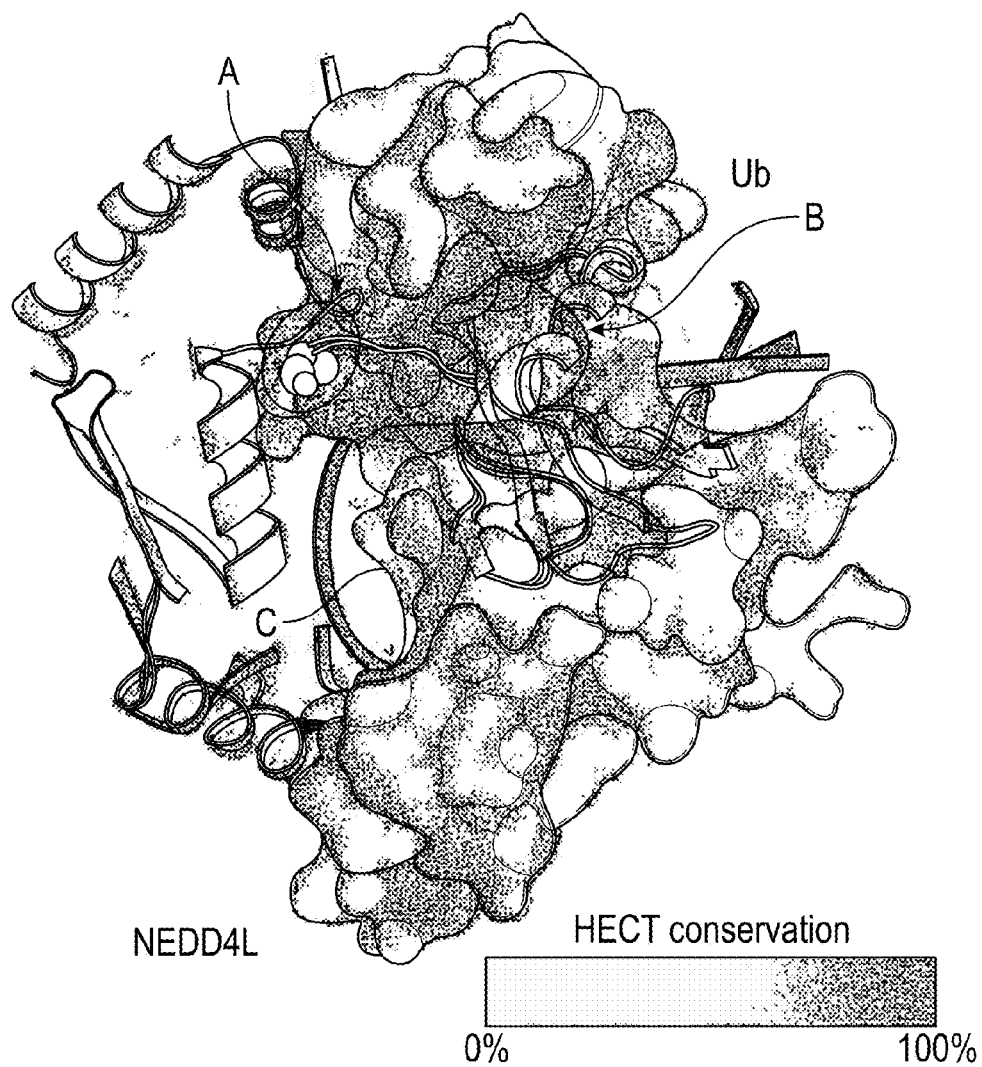
FIG. 2 depicts an activity probe. A ubiquitin conjugating peptide (e.g. E2) forms an interaction domain with a ubiquitin ligase (e.g. E3) (arrow A), a reactive chemical moiety reacts with the cysteine in the active site of the ubiquitin ligase (arrow B) and a ubiquitin peptide (arrow C).
Figure 3B:
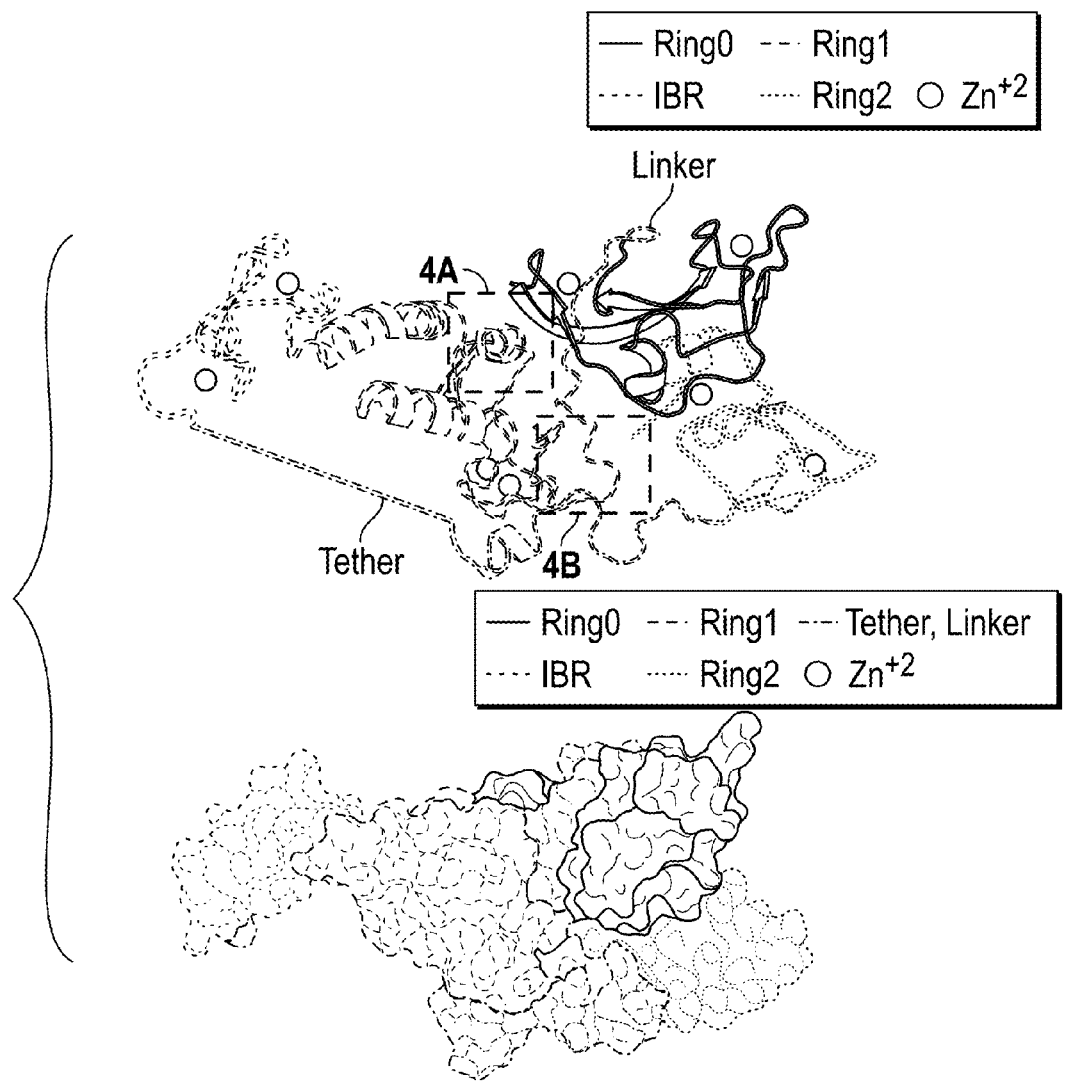
Figure 3C:
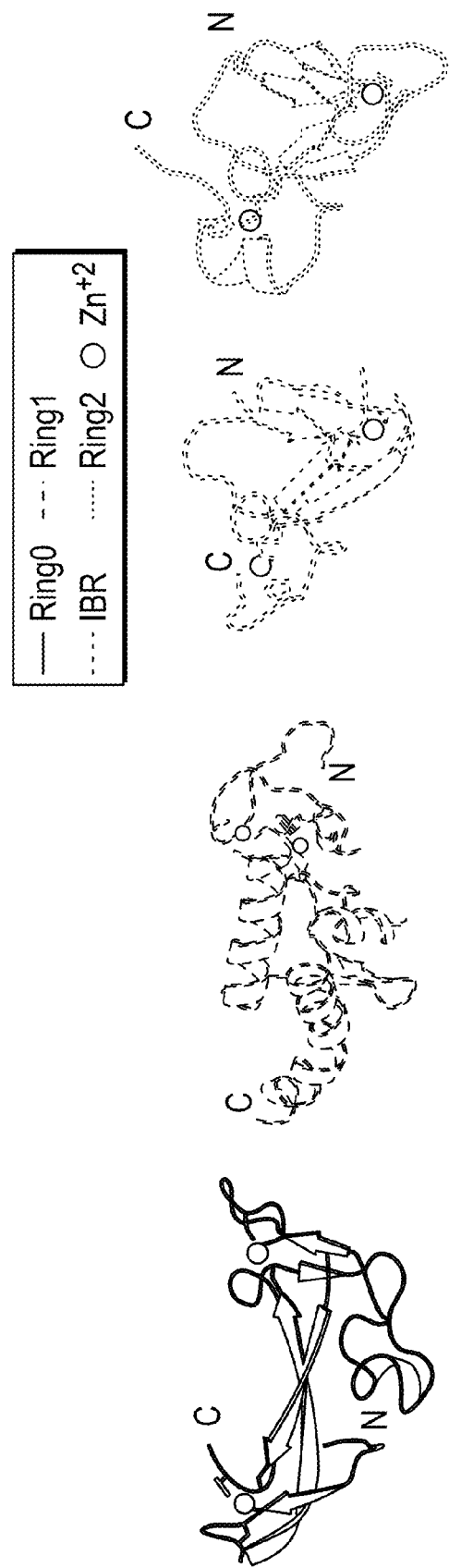
Figure 4A:
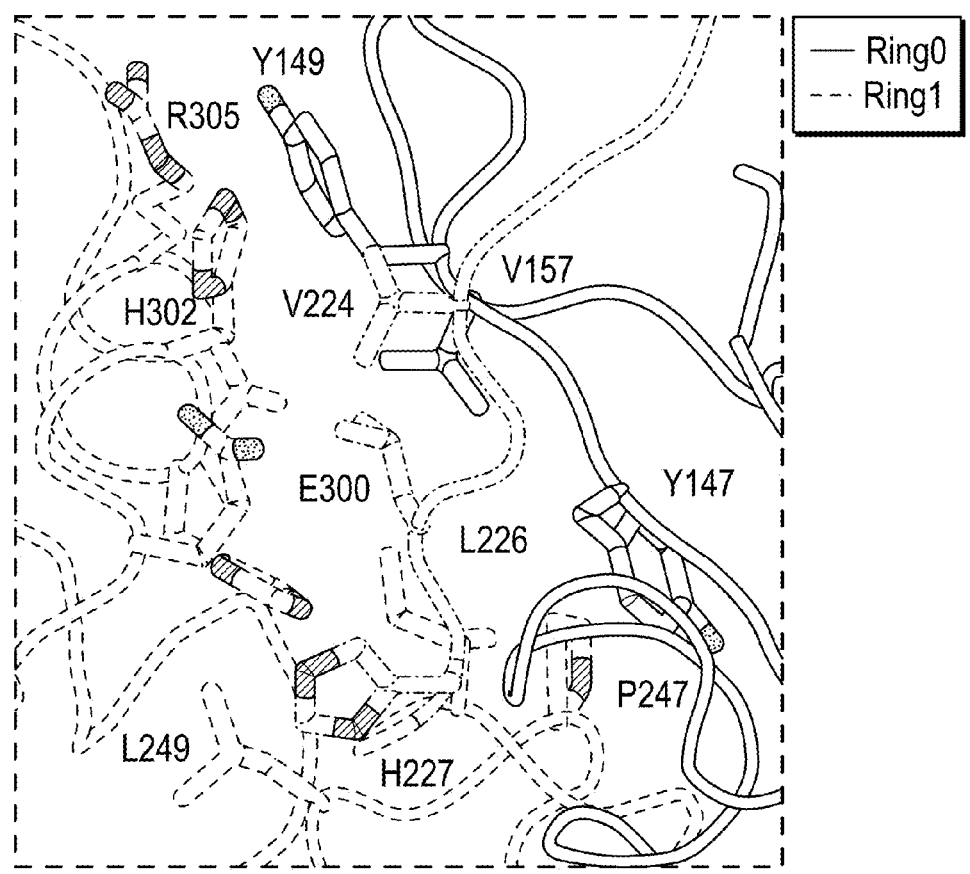
FIG. 4 shows that R0RBR is assembled into two compact domain groups separated by linkers. A. The R0 and R1 interface is relatively hydrophilic and separated by the R0-R1 linker, suggesting this area may have some structural flexibility. B. The tether residue W403 sits in a hydrophobic pocket on R1 and may serve as a 'pin' to anchor the two turn helix of the tether to R1. W403 also forms a hydrogen bond with the terminal carboxylate of V465. R256 is the site of a human PD mutation. C. The R0 domain forms a hydrophobic interface with the catalytic domain R2, inserting residues W462 and F463 into the hydrophobic core of R0. The catalytic cysteine, C431, is adjacent to this interface.
Figure 4B:
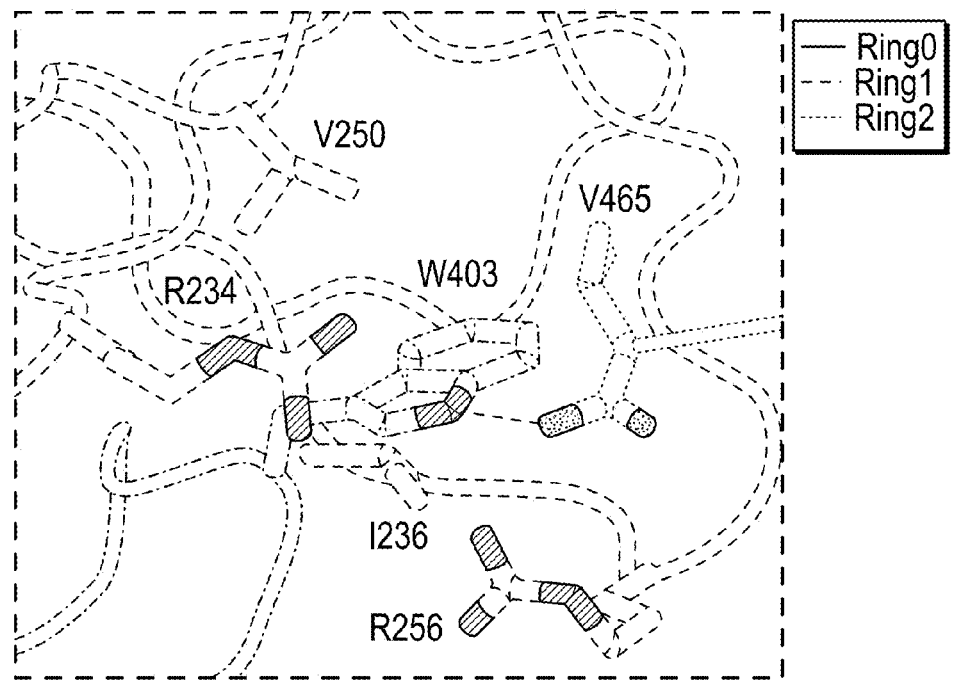
Figure 4C:
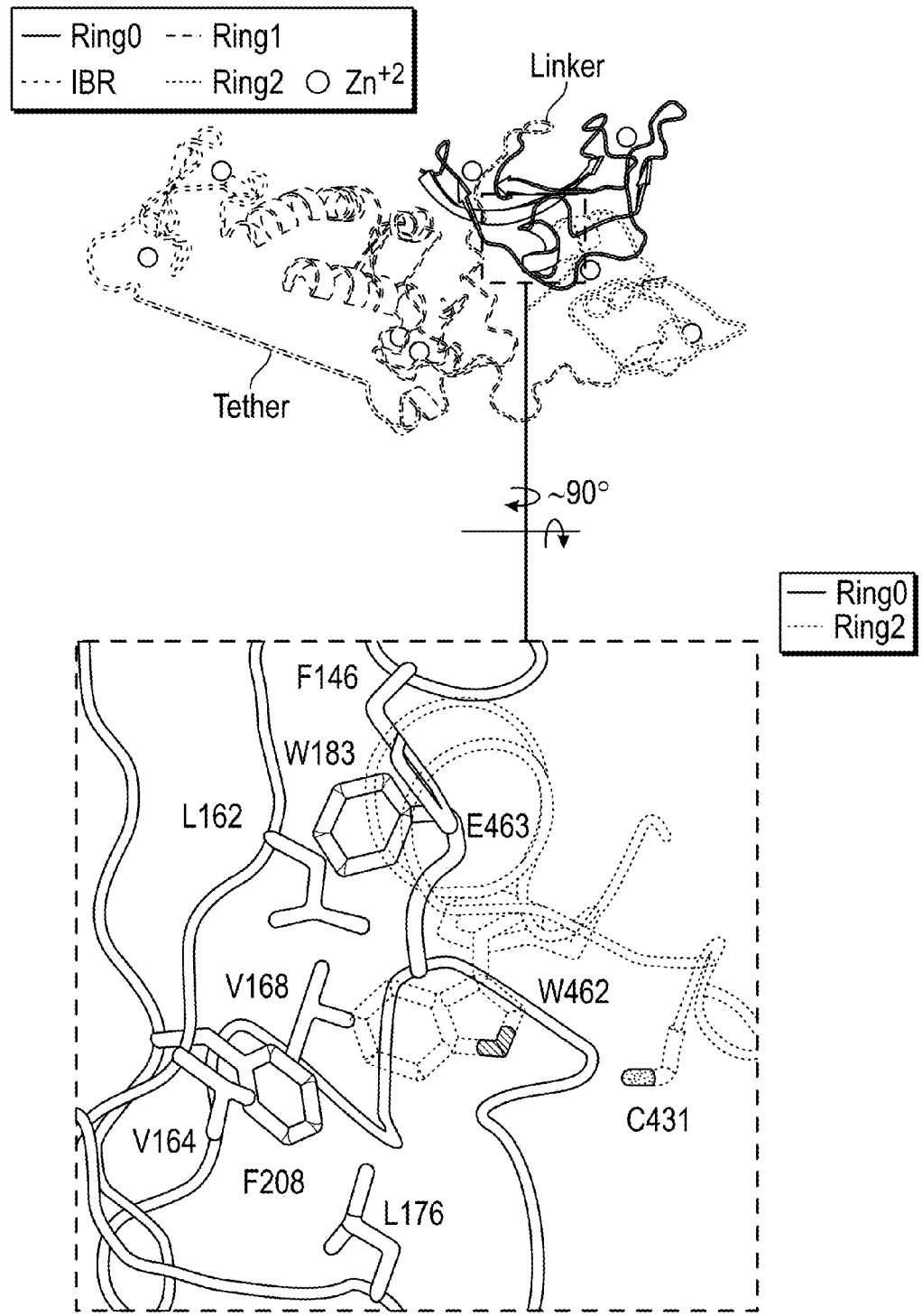

The overall R0RBR structure reveals two compact domain groups separated by two linkers (FIG. 3b). One domain is comprised of an association between RING1 (R1) and IBR formed by a small hydrophobic patch at their interface boundary. Since R1 has a canonical RING structure, it can be visualized as the binding site for E2 based on the structure of other RING ligases. The other domain is formed by close association of R0 and R2, involving a total of ~1330 Å$^2$ surface area between the C-terminal region of R2 and the hydrophobic core of R0 (FIG. 3b, 4c). R2 contains the proposed catalytic cysteine (C431) that is near the hydrophobic interface with R0. The R0:R2 interface is unique to Parkin since it involves sequences within R0 as well as the C terminus of R2 that are distinct from other RBR ligases. The R0-R1 linker region between the two major domains has a coil conformation and resides in a relatively hydrophilic interface (FIG. 4a), suggesting that this may be an area of potential structural flexibility. The IBR-R2 linker region (which is referred to as the tether: residues 378-414) is 37 residues long. Most of the beginning of the tether (14 residues) is disordered, while the latter part runs across the surface of R1. The tether forms significant interactions with R1, but is also an area of potential flexibility. A two turn helix (residues 394-401) packs against R1 and the nearby residue W403 may serve as a 'pin' to anchor the tether to R1 and associate it with R2 (FIG. 2b). The side chain of W403 sits in a hydrophobic pocket formed by several R1 residues and forms a hydrogen bond with the terminal carboxylate of V465 a residue only found in mammals. As described above, R1 is a likely E2 binding site on Parkin and the position of the tether has the potential to regulate this interaction (FIG. 4b).

To interrogate the accessibility of Parkin's catalytic machinery without the confounding factors that result from the interactions of E2 in a transthiolation reaction, the activity probe Ub-vinyl sulfone (Ub-VS) was used. Ub-VS is a specific probe that will covalently modify the active site cysteine of DUBs and HECT ligases through specific recognition of Ub and the oriented positioning of the VS moiety. The R0RBR domain of Parkin weakly reacted with Ub-VS, while the RBR domain of Parkin produced a ~8 kDa shift in molecular weight indicating that the RBR domain of Parkin is more reactive to probe than the R0RBR. N-terminally SUMO-tagged R0RBR was also active in this assay (FIG. 5a). These results suggest that removal or modification of R0, which is closely aligned with R2, may allow conformational changes near the active site to facilitate probe reactivity. The intensity of Ub-VS probe labeling has been suggested to correlate with the functional state of the active site of the enzyme and in support of this idea we found that autoubiquitination activity was consistent with probe binding (FIG. 5a). Furthermore, these results are consistent with recent published work demonstrating greater levels of activity for RBR compared to R0RBR Parkin constructs. Using mass spectrometry we confirmed the Ub-VS was attached only to Parkin's C431, and confirmed labeling of Parkin was specific for Ub-VS since other Ub-like VS moieties did not robustly label Parkin. While there is an example of a ligase (A20) that also has DUB activity, this is not the case for Parkin and is not likely to be the reason that Parkin can be labeled with Ub-VS probe.

In transthiolation reactions, the active site cysteine needs to be activated for nucleophilic attack of the E2-Ub thioester carbonyl bond. Activation of the cysteine and stabilization of the resulting tetrahedral intermediate require the presence of characteristic elements found in cysteine proteases or DUBs: an activating catalytic dyad or triad, and an oxyanion hole framed by backbone or sidechain hydrogen bond donors. Examination of the residues surrounding Parkin's active site C431 revealed putative active site triad residues consisting of C431, H433 and E444 (FIG. 5b). These residues are conserved across all species of Parkin examined, and mutation of F1433 and E444 significantly disrupted Ub-VS probe reactivity at neutral pH (FIG. 5c), and reactivity was completely eliminated by mutation of C431 (FIG. 5a, c). The role of histidine within a catalytic dyad or triad is to function as a base that deprotonates the cysteine for activation—a role that can potentially be obviated by elevated pH. Consistent with this mechanism, it was found that while H433A or H433N demonstrated little probe reactivity at neutral pH, probe labeling was restored with pH titration (FIG. 5c). As is common for DUBs, in this structure C431 and H433 are not well aligned for catalysis and implies that a conformational rearrangement must occur for catalysis to take place (FIG. 5b).

Figure 6A:
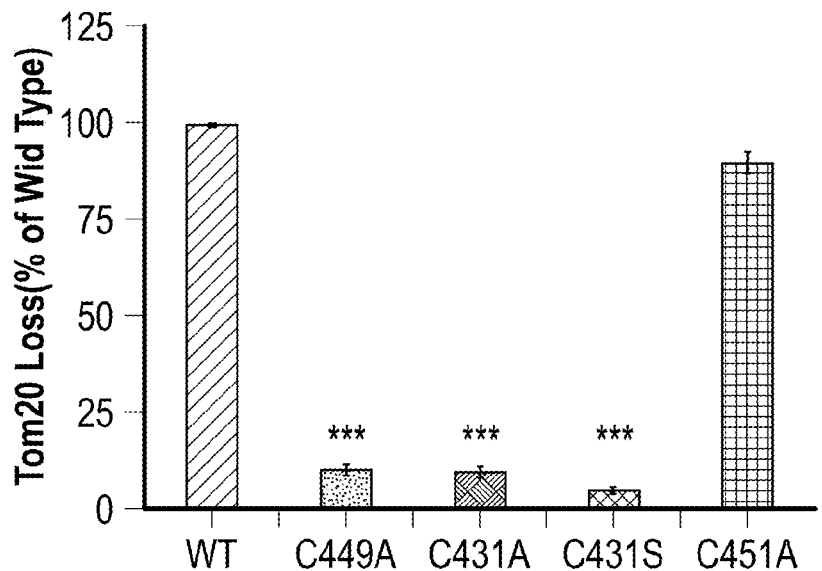
FIGS. 6*a-f* demonstrate that mitochondrial stress activates Parkin and drives exposure of the active site C431. A. Parkin active site mutants C431S/C431A compromise Parkin's ability to decrease cellular Tom20 levels. B. Western blot showing formation of ~8 kDa Parkin immunoreactive species during mitochondrial stress (CCCP) only in cells expressing full length Parkin C431S. C. Western blot showing the ~8 kDa Parkin immunoreactive species is sensitive to sodium hydroxide treatment indicative of Ub oxyester formation on full length Parkin C431S. D. Enhanced cellular activity of full length Parkin F463Y compared to full length wild type Parkin. E. Autoubiquitination of R0RBR F463Y is increased compared to wild type R0RBR. F. Increased HA-UbVS probe labeling of R0RBR F463Y compared to wild type R0RBR.
Figure 6B:
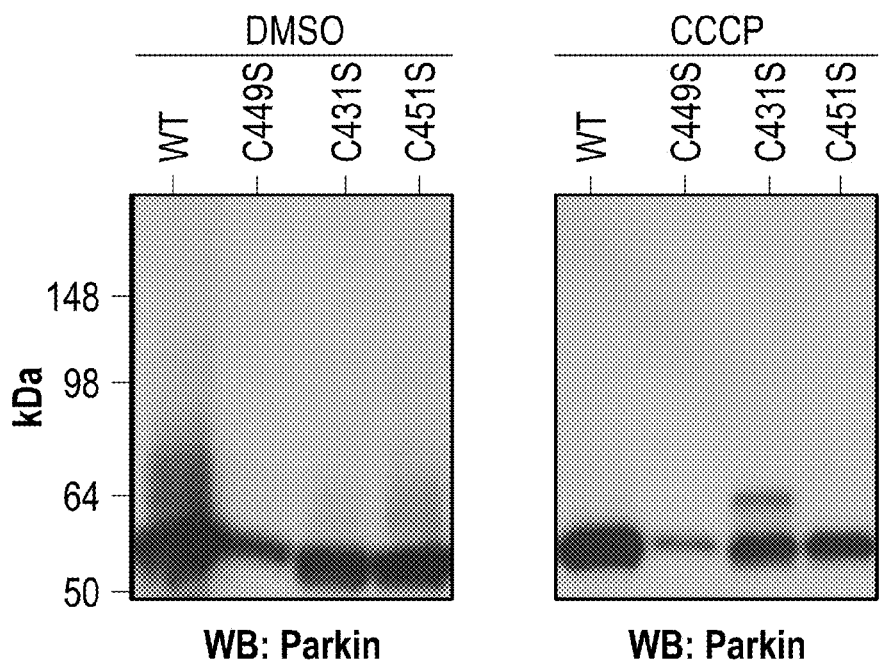
Figure 6C:
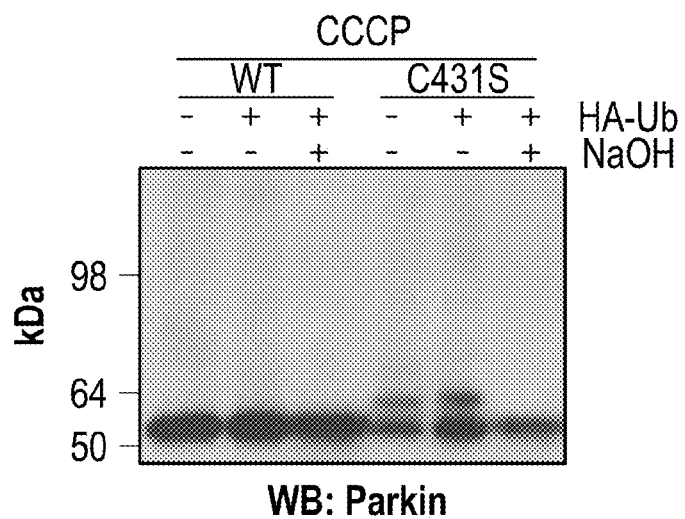

In cells, Parkin has been shown to play an important role in Parkin-catalyzed degradation of mitochondrial protein, following treatment with mitochondrial toxins, such as CCCP. To assay functional activity of C431 in cells, Tom20 loss was examined as a measure of Parkin-catalyzed degradation of mitochondrial protein, following CCCP treatment. While Mitofusions and other mitochondrial proteins have been reported to be Parkin substrates, Tom20 loss here was a highly reproducible Parkin-dependent event after CCCP treatment. The active site cysteine mutants, C431S and C431A, while soluble and well-behaved, were unable to function in this cellular assay (FIG. 6a), consistent with the utilization of Parkin's active site C431 during mitochondrial stress. Moreover, it was demonstrated that the C431S mutant formed an Ub oxyester only in the presence of CCCP, directly supporting C431 as an active site residue in cells (FIG. 6b, c) and that Parkin has latent activity that can be activated by CCCP. Although, there is the formal possibility that C431 is also involved in translocation of Parkin to mitochondria. Mutation of H433 and E444 in our cellular assay, revealed a requirement for H433, but no requirement for E444 even though neither mutation affected protein levels. Why E444 is dispensable in cells is not clear, although Parkin may have a binding partner in cells that provides the role of the Glu in positioning the His, or the pH at the mitochondria membrane may be such that the E444 is dispensable for deprotonation of C431. While the Cys, His and Glu residues are completely conserved across all species of Parkin, the motif is not conserved across all RBR ligases, and other RBR ligases may use a different catalytic mechanism.

Figure 6D:
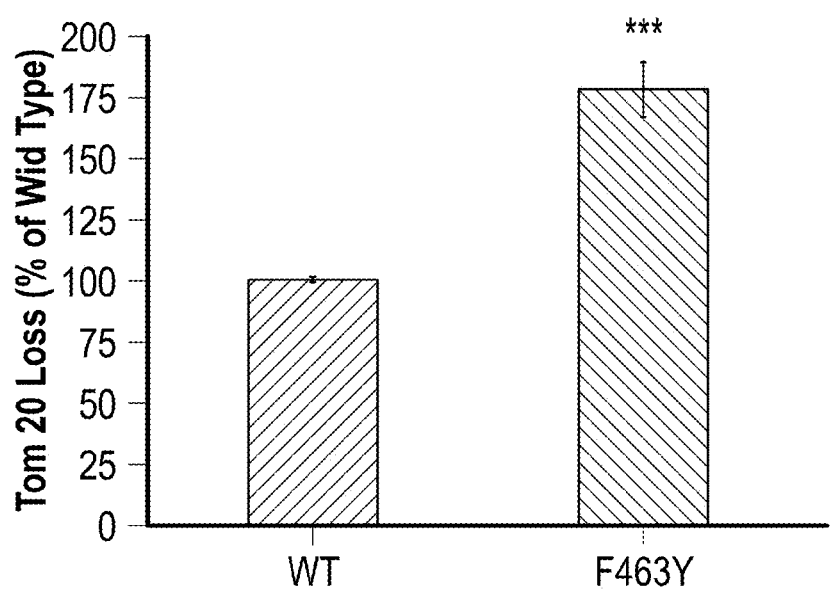
Figure 6E:
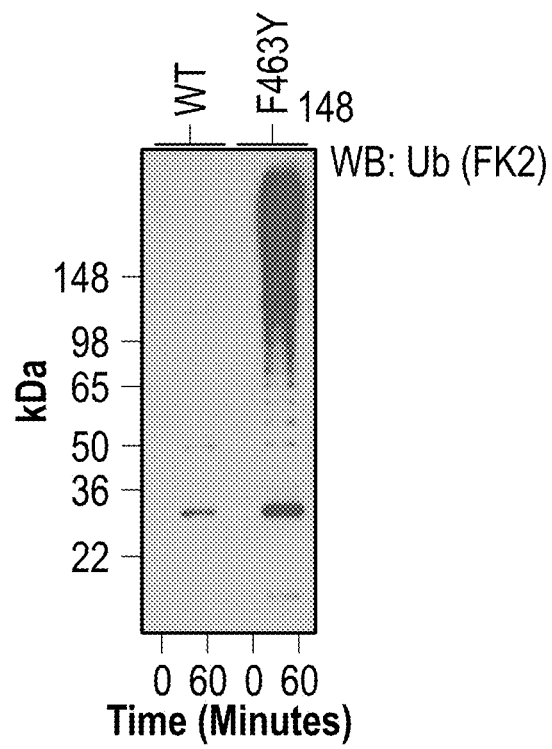
Figure 6F:
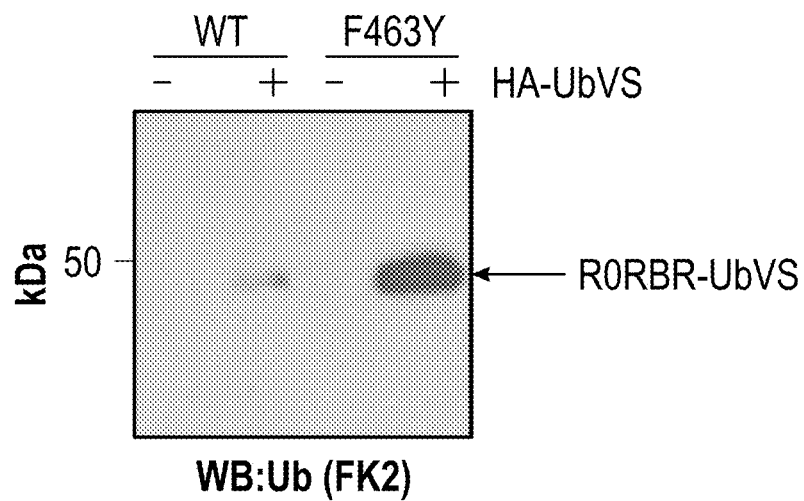

Inspection of the extreme C-terminus of Parkin revealed a conserved phenylalanine (F) at the −3 position, F463, and Phe at the −5 to −3 position has been described as a critical determinant for positioning of the incoming substrate lysine in HECT ligases Mutation of F463 to tyrosine (FIG. 6d) enhanced the activity of Parkin in cells for Tom20 loss as well as dramatic increases in autoubiquitination activity and Ub-VS probe binding of R0RBR in vitro (FIG. 6e, f). This suggests that the conserved F463 at the extreme C-terminus of Parkin is likely to serve in a distinct capacity from the extreme C-termini of HECT ligases structurally described thus far. In our structure, F463 is involved in critical hydrophobic interactions predicted to contribute to integrity of R0:R2 interface (FIG. 4c), coupled with the data above, this result suggests that the R0:R2 interface defined in the Parkin structure is important in regulation of Parkin's active site. In fact, mutation of any of the hydrophobic residues that comprise the R0:R2 interface results in increased autoubiquitination activity. Thus, the −3 Phe in Parkin functions distinctly from similarly spaced residues in other HECT ligases, and suggests that it is possible to increase Parkin activity through changes in the integrity of the R0:R2 interface.

Figure 7A:
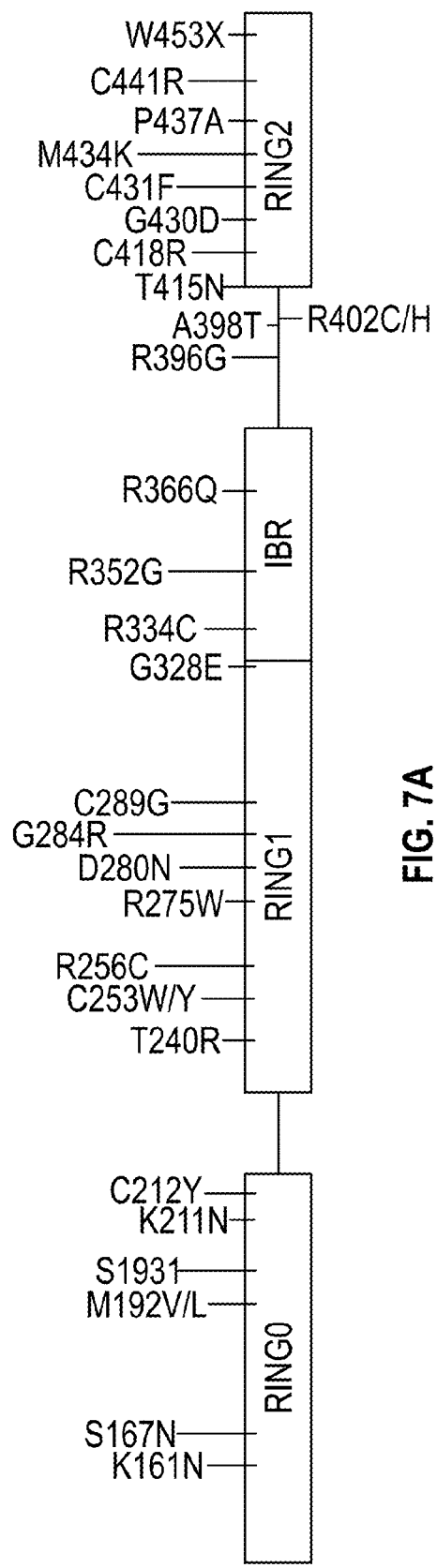
FIGS. 7*a-b* show human genetic PD mutations mapped on Parkin-R0RBR. A. Schematic diagram of Parkin-R0RBR indicating residues that can be mutated in PD. B. R0RBR ribbon representation (left) and space filling model (right)
Figure 7B:
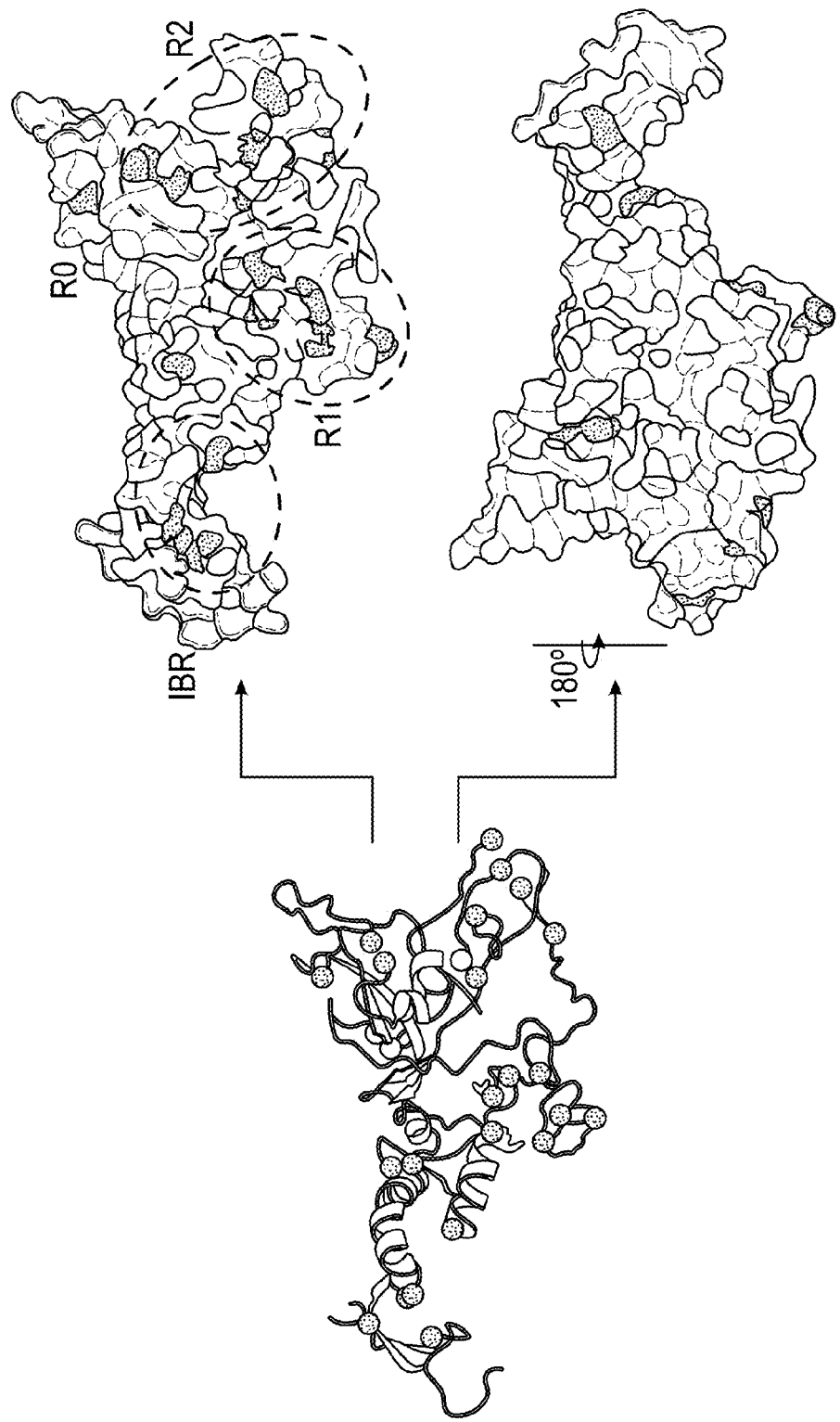

Twenty-eight (of the approximately seventy) human genetic mutations in Parkin were selected that represented an unbiased distribution throughout the various Parkin domains (in R0RBR) for mapping analysis in our structure. Examination of these mutations in Parkin revealed that ten mapped to residues directly involved or closely aligned with Zn coordination. The other mutations are present in each of the four domains and the tether (FIG. 7), and can be roughly grouped into two functional regions; E2 binding and the area surrounding the catalytic cysteine. There are three PD mutations (R396G, A398T, R402C/H) that occur in the linker closely associated with R1 in the region of the short a-helix of the tether, and A398T would be predicted to directly perturb the interaction with R1 and have implications for E2 binding. Furthermore, the R1 mutation T240R may interrupt E2 binding as was reported experimentally. Mutations in the IBR domain and at the R1:IBR interface could disrupt structural integrity and E2 binding. Finally, numerous mutations occur around the catalytic C431, these mutations might disrupt substrate/cofactor binding or catalytic efficiency.

The structure of Parkin R0RBR was solved at high resolution. Overall, this structure demonstrates characteristics of RING and HECT ligases, as has been suggested by previous biochemical analysis of HHARI. Analysis of this structure reveals several new aspects of the Parkin protein including: novel RING structures for R0 and R2, insight into the catalytic activity at the molecular level, unpredicted interfaces between domains, and a clustering of human PD mutations that were not indicated from linear mapping studies.

The individual RING domains for Parkin have been the subject of much debate, in regards to the specific residues that coordinate Zn ions, as well as their relationship to canonical RING cross-brace structures defining classical E2 binding domains. R1 is the only RING domain of Parkin that demonstrates a typical E2 binding motif, with a cross-brace structure that defines this domain. R0 is a novel domain structure, but is more similar to Zn-finger domains than to E3 RING domains (FIG. 1). The IBR domain is largely as predicted from high-quality NMR studies of the isolated IBR domain from Parkin. RING2 is similar to the IBR domain of Parkin and HOIP. However, neither resembles canonical RING domain motifs, as they do not have a cross brace structure. These findings call-into question whether the RING nomenclature is actually appropriate for the R0, IBR and R2 domains.

Previous work defining RBR ligases as RING/HECT hybrids predicted a HECT-like catalytic cysteine residue in the R2 domain. While the R2 domain does not resemble a typical HECT structure, our analysis confirmed that there is a catalytic cysteine at C431. Similar to what has been found with Parkin, a series of bacterial ligases have recently been described that function through a catalytic cysteine residue, but bear no sequence or structural similarity to HECT domains. Thus, bacterial ligases, RBR ligases and HECT ligases function through a catalytic cysteine, but are structurally and sequence-wise distinct:

Mechanistically, residues were identified in the catalytic core that may function with C431 to promote catalysis. Mutational studies of H433 and E444 demonstrated that H433 is required to promote catalytic activity through C431 in vitro and in cells. Whether this finding is representative of a catalytic triad/dyad mechanism as has been demonstrated for DUBs or whether it represents a mechanism that functions through an hydrogen bonding network with other residues remains to be determined through more extensive mutational analysis. However, the use of the Ub-VS probe clearly demonstrates that H433 is involved in the transthiolation step from E2 to E3 at C431. Importantly, the access to C431 may be restricted, and serve as a means to regulate Parkin activity.

The R0RBR structure reveals that the molecule is folded in half with the N- and C-termini forming an extensive interface that comprise two compact domain groups separated by two linkers (FIG. 3b). One domain group is comprised of an association between R1 and IBR, the other domain group is formed by a close association of R0 and R2. The R1:IBR domain group contains the putative E2 binding site, which appears to be obstructed by a portion of the IBR, that we have designated the 'tether'. Mutational analysis of this tether region, including W403, is likely to yield important insight into activation of Parkin in regards to E2 access. A key feature of the R0:R2 domain group is the positioning of the C-terminus of Parkin R2 into a hydrophobic region on R0. The R0:R2 interface may contribute to regulation of Parkin activation in two ways: By restricting access of the incoming Ub C-terminal Gly-Gly to Parkin C431, and by misalignment of Parkin's catalytic machinery, namely H433 and C431. The functional analysis of the R0:R2 interface demonstrated that mutation of individual hydrophobic residues resulted in activation of Parkin autoubiquitination, and probe label (FIG. 6). Because probe label depends upon access to the active site, and appropriate alignment of catalytic residues, this result suggests that R0:R2 interface mutations likely function in one or both of the two ways suggested above. An increased Ub binding was not observed in these mutants by Biacore, suggesting they do not function to increase affinity for Ub. In our structure, H433 is involved in water-mediated hydrogen bonding with W462 and is not available to deprotonate C431 (FIG. 5c), representing an inactive state of the enzyme through misalignment of the catalytic residues.

Notably, mutation of F463 does not result in loss of Parkin activity. In other HECT ligases, a similarly spaced phenylalanine is thought to position the E3 ligase thioester-bound Ub for transfer to substrate, and is critical for activity. Thus, while Parkin exhibits catalytic cysteine activity similar to HECT ligases, it is also functionally distinct, since the −3 Phe appears to function in a different capacity. Finally, the movement within the interface between the two large domains formed by R1:IBR and R0:R2 may provide a way in which to juxtapose the catalytic cysteine of UbcH7 (bound to R1) with the active site C431 in the R2 of Parkin. in our current model, E2 (UbcH7) bound to Parkin is too distant for transthiolation of C431 to occur. The structure suggests the potential for a conformational change to facilitate transthiolation from UbcH7 to Parkin. It is envisioned that this movement to be that of a butterfly motion whereby R1:IBR and R0:R2 move with respect to each other via the flexible linker and tether regions shown in beige (FIGS. 3b,c, and 4a). However, a full mutational analysis of these interfaces, and a structural determination of Parkin bound to UbcH7 during transthiolation, will be necessary to address this issue. Such studies have been done for other ligases, and have demonstrated linkers that promote and allow for considerable conformational flexibility. This structural analysis and mapping of PD mutations of Parkin demonstrates that there are key functional areas on Parkin that are affected by mutations. Largely, the mutations cluster into three groups: 1. Zn coordination residues, likely to affect overall structural stability; 2. Predicted E2 binding region, with mutations in the direct binding site for the E2, as well as in regions proximal to the predicted E2 binding site that may affect movement of the tether residues or aspects that are still not yet understood about E2-E3 binding interactions; and 3. The catalytic region around residue C431. This map will be highly useful in future investigational studies of the functional role for these mutations in catalysis, E2 binding, conformational flexibility, activation of a latent state, as well as potential regions for critical binding partners. Functional studies have also defined key features of isolated Parkin mutations and some of these mutations may help identify regions of Parkin that are important for localization to mitochondria. The fact that the mutations mapped in this study largely occur on one face of the molecule is suggestive of a specific functionality for a directed orientation relative to other molecules. Prior to this study, it was very difficult to understand Parkin mutations in an overall picture, but this structural snapshot will provide a map for testing new hypotheses.

This structural, biochemical and cellular data indicate that Parkin functions as a RING/HECT hybrid. Parkin likely binds E2 through a conserved structural motif on a canonical RING domain, and also functions through a HECT-like active site cysteine whose activity can be regulated through interaction between the R0 and R2 domains. This structure of Parkin R0RBR will be useful for drug discovery efforts aimed to increase ligase activity, as well as to elucidate the molecular mechanisms of ubiquitination in this new class of E3 ligase.

Methods

General Reagents and DNA Constructs

The DNA template for all Parkin constructs was NM_004562 and NM_004562.1. For bacterial expression full length Parkin (1-465), R0RBR (141-465) and RBR (238-465) were cloned into Champion pET SUMO vector per the manufacturer's instructions (Invitrogen). For mammalian expression Parkin (untagged full length) was cloned into pcDNA3.1. All mutations were created using QuikChange Site-Directed Mutagenesis Kit (Agilent Technologies). For western blotting all antibodies were used at 1:1000 per the manufactures recommendations. Anti-Parkin Ab (Prk8) was from Sigma. Anti-Parkin Ab (HPA1A) was a rabbit polyclonal Ab that was raised against an N-terminal peptide of Parkin (a.a. 85-96). Anti-GAPDH Ab was from Millipore. Anti-Ub Ab (FK2) was from Enzo Life Sciences. Rabbit anti-Tom20 Ab was from Santa Cruz. Alexa 594 and Dapi were from molecular probes (Invitrogen). Mouse anti-HA Ab was from Covance. CCCP was from Sigma. El, UbcH7, UbcH8, Ub, Mg-ATP solution were all from Boston Biochem. HA-UbVS and all other Ub-like-VS were from Boston Biochem. The Anti-FLAG M2 agarose resin and the 3× FLAG peptide were obtained from Sigma Aldrich. Protein A beads were from Repligen.

Protein Expression

Bacterial expression constructs were transformed into BL21 DE3 *E. Coli* (Invitrogen). Overnight cultures inoculated from fresh colonies were grown in Terrific broth media containing 2% glucose and 50 µg/ml kanamycin at 37° C. The following morning overnight cultures were diluted to OD600 0.1 and continued shaking at 37° C. until $OD_{600}$ reached 0.4, flasks were then transferred to 16° C., upon $OD_{600}$ 0.8 to 0.9, cultures were induced with 0.1 mM IPTG supplemented with 50 µM zinc chloride and expression was allowed to proceed for 18-20 hours at 16° C. Cells were then harvested by centrifugation and frozen at −80° C.

Protein Purification

High performance Ni sepharose, the Mono Q HR 10/10 anion exchange column, and the HiLoad 26/60 Superdex 200 column were all from GE Life sciences. FPLC was performed on an AKTA FPLC system. UV-Vis absorbance readings were taken on a Nanodrop spectrophotometer. Protein was analyzed by SDS-PAGE under denaturing conditions on 10% Bis-Tris NuPAGE gels using MES running buffer (Invitrogen). The extinction coefficients (s) for the denatured proteins were determined from the primary sequence, according to e=5690 cm$^{-1}$M$^{-1}$×(number of trp)+1280 cm$^{-1}$M$^{-1}$×(number of tyr)+120 cm$^{-1}$M$^{-1}$×(number of cys–where cys=cystine or disulfide bond).

For purification of SUMO-Parkin constructs from bacteria, cells were resuspended in buffer A (50 mM Tris pH 8.0, 200 mM NaCl, 10 mM imidazole, 250 µM TCEP, and EDTA-free Complete protease inhibitor tablets (Roche)) and lysed using a microfluidizer. The lysate was cleared (45,000 g, 25 min, 4° C.) and the supernatant agitated gently with high performance Ni sepharose (0.625 ml resin/L cell culture) for 1 hr at 4° C. The beads were washed with 10 column volumes of buffer A containing 20 mM imidazole and then washed with 10 column volumes of buffer A containing 40 mM imidazole. The protein was eluted with 10 column volumes of buffer A containing 200 mM imidazole. After elution, the protein was dialyzed into 50 mM Tris for 2 h at 4° C. to reduce the salt concentration. The protein was then loaded onto a Mono Q HR 10/10 anion exchange column that had been pre-equilibrated in buffer B (50 mM Tris pH 8.0 and 250 µM TCEP). The column was developed with a gradient of 0-500 mM NaCl over 50 column volumes and the protein was eluted at 113-180 mM NaCl. Collected fractions were then concentrated and injected onto a HiLoad 26/60 Superdex 200 column that had been pre-equilibrated in buffer C (25 mM HEPES pH 8.0, 50 mM NaCl, and 1 mM TCEP). The column was eluted with 1.5 CV of buffer C.

For removal of the SUMO tag, purification was as described above except after the Mono Q column protein was incubated with SENP1 (10:1 w/w ratio of protein to SENP1) for 2 h at 4° C. Following the incubation, 10 mM imidazole was added to the cleavage reaction and the reaction was purified over a high performance Ni sepharose column (0.625 ml resin/L cell culture). The Ni column was washed with 10 CV of buffer A. Both the wash and the flowthru from the Ni column were collected and injected onto a HiLoad 26/60 Superdex 200 column that had been pre-equilibrated in buffer C (25 mM HEPES pH 8.0, 50 mM NaCl, and 1 mM TCEP). The column was eluted with 1.5 CV of buffer C.

Crystallization and Structure Determination

Parkin R0RBR-P223 protein crystals were grown in sitting drops containing 0.3 µL each of 12.5 mg/mL protein in 25 mM HEPES (pH 8.0), 50 mM NaCl, and 1 mM TCEP and a reservoir of 0.1 M HEPES (pH 7.5), 20% PEG 4K, 10% isopropanol, 10 mM $BaCl_2$ at 10° C. Seeding was used to obtain higher quality crystals and crystals generally reached full size in 4-7 days. Crystals were transferred to 15% ethylene glycol in reservoir solution before being flash cooled in liquid nitrogen. The crystals belong to the space group $C222_1$ (a=86.96 Å, b=133.16 Å, c=65.39 Å) and contain one molecule per asymmetric unit. Synchrotron x-ray data were collected on a single crystal at a peak/inflection compromise and remote wavelengths in order to measure the Zn anomalous and dispersive signals. Diffraction data were integrated with MOSFLM and scaled with SCALA. Nine anomalous sites were found by SHELXD and phases were refined with MLPHARE. Solvent flattening against high-resolution data (1.58 Å) collected at 1.1159 Å using DM resulted in a clearly interpretable electron density map. The mean figure of merit was 0.217 after MLPHARE and 0.715 after solvent flattering. The model was built manually into this map using the program Coot. One of the anomalous sites was modeled as barium based on the characteristics of the coordinating ligands. The structure was refined against the high-resolution data using REFMAC, and contains 306-aa residues and 267 water molecules. Both structures have been deposited in the protein data bank, pdb codes 4I1F (Parkin R0RBR-P223) and 4I1H (Parkin R0RBR-5223).

Parkin R0RBR-S223 crystals were grown in sitting drops using 0.3 µL each of 10 mg/mL protein in the same buffer as Parkin R0RBR-P223 and a reservoir of 0.1 M TRIS (pH 6.5), 0.2 M NaCl, and 25% PEG 3350 at 10° C. The crystals grew over 3 days and then were transferred to 10% ethylene glycol in reservoir solution before being flash cooled in liquid nitrogen. Crystals belonged to $C222_1$ (a=87.11 Å, b=133.9 Å, c=66.21 Å). Data were collected using a home source Saturn 944 detector and Rigaku MicroMax007HF generator, processed with MOSFLM and scaled with SCALA. The Parkin-R0RBR-P223 structure was used as a starting model and rebuilt as necessary in Coot, alternating with rounds of refinement to 2.0 Å in REFMAC, and the final model contains 306-aa and 263 waters.

Biochemical Assays

Parkin autoubiquitination reactions were typically carried out in a 25 µl reaction volume in reaction buffer of 50 mM HEPES, 50 mM NaCl, pH 8.0 for 1 h at 37° C. using E1 (250 nM), E2 (5 µM) Ub (23.5 µM), Mg-ATP solution (10 mM) and Parkin species (0.46 µM). Reactions were terminated by the addition of SDS loading buffer.

Parkin activity-probe labeling with HA-UbVS. Briefly Parkin (5 µg) was incubated with HA-UbVS (or other Ub-like VS, Boston Biochem) at 3:1 Parkin:UbVS molar ratio or at 1:1 Parkin:UbVS ratio for 3 h at room temperature in 50 mM HEPES, 50 mM NaCl, over a range of pH. Reactions were terminated by the addition of SDS loading buffer.

Parkin Cellular Assay

Cells were stained as previously reported with the exception that cells were typically grown in 24 well plastic dishes. Images were captured on the Cellomics ArrayScan VTi platform (Thermo Scientific) using the Target Activation BioApplication to quantify the percentage of cells containing Tom20 mitochondrial staining. Cell fields were imaged using a 10× objective lens with an average of 250 cells detected per field. Data were collected from at least 2000 cells per well of a 96-well plate. The readout parameters for the cellular assay were average fluorescence intensity and the percent of cells showing little or no Tom20 staining. The percentage of Tom20 loss relative to full-length wild type Parkin was calculated by setting full-length wild type Parkin-induced Tom20 loss after CCCP treatment to 100%. Data presented is representative of three to four independent experiments (error bars represent s.e.m.).

Statistical Analysis

Triple asterisk denotes P<0.005, double asterisk denotes P<0.01 and single asterisks denote P<0.05. The significance levels were determined using the heteroscedastic Student's t-Test with two-tailed distribution. Cells were transfected with XtremeGene according to the manufactures protocol (Roche) using untagged full length Parkin (or mutants) together with HA-Ub with a DNA ratio of 1:10 respectively. Transfections were for 48 h with media exchange and addition of CCCP (10 µM final) after 24 h. Cells were lysed on ice for 30 minutes in 20 mM HEPES, 150 mM NaCl, 10% glycerol, 1% Triton-X-100, pH 7.2 with EDTA-free complete protease inhibitors (Roche). Lysates were clarified for 10 minutes at 16,000×g in a tabletop microcentrifuge at 4° C. Protein was quantified using BCA (Thermo Fisher Scientific). To obtain sufficient separation of Parkin and the oxyester-linked Parkin, samples were typically run for 2 h on a 10% Tris-Glycine gel (Invitrogen). For immunoprecipitation of oxyester-linked Parkin, one mg of protein extract (after a one hour preclear with protein A beads alone) was incubated with Protein A resin and HPA1A (5 µM) overnight with rotation at 4° C. The next day samples were washed 3× with lysis buffer followed by addition of SDS loading dye. Reactions were then incubated with NaOH (0.14 mol/L) or buffer control for 20 minutes at 37° C. before being boiled.

Mass Spectrometry

For LC-MS/MS identification of Parkin-C431-UbVS modified peptide tryptic digests of Parkin reacted with. HA-UbVS were analyzed on an ABSciex 5600 qTOF mass spectrometer using a method in which each survey MS scan was followed by MS/MS analysis of the 30 most abundant peaks in the MS spectrum. Identification of peptides was performed using Mascot version 2.4, with 10 ppm for peptide mass tolerance, and 0.1 Da for MS/MS tolerance. To determine the peptide identifications the Uniprot database was searched using oxidation (M±15.9949 Da), deamidation (1\1Q±0.9840 Da), carbamidomethylation (C±57.0214 Da), and the GG-vinyl sulfone remnant (C±192.0569 Da) as variable modifications.

Although the invention has been described with reference to the above examples, it will be understood that modifications and variations are encompassed within the spirit and scope of the invention. Accordingly, the invention is limited by the following claims.

What is claimed is:

1. An activity probe comprising:
   a) a ubiquitin conjugating peptide;
   b) a reactive chemical moiety; and
   c) a ubiquitin peptide.

2. The activity probe of claim 1, further comprising a label.

3. The activity probe of claim 1, further comprising an epitope tag.

4. The activity probe of claim 1, wherein the ubiquitin conjugating peptide is an E2 peptide.

5. The activity probe of claim 4, wherein the E2 peptide forms an E2-E3 interaction domain.

6. The activity probe of claim 1, wherein the chemical moiety reacts with the active site cysteine of a ubiquitin ligase.

7. The activity probe of claim 1, wherein the chemical moiety is selected from the group consisting of acrylates, vinyl sulfonyls, acyloxymethylketones, beta-lactones, cyanamides and epoxysuccinates.

8. The activity probe of claim 1, wherein the ubiquitin peptide contains a E3-Ubiquitin interaction domain.

9. The activity probe of claim 1, wherein the ubiquitin conjugating peptide is selected from the group consisting of SEQ ID NO:1, SEQ ID NO:2, SEQ ID NO:3, SEQ ID NO:4 and SEQ ID NO:5.

10. The activity probe of claim 1, wherein the ubiquitin peptide is selected from the group consisting of SEQ ID NO:6, SEQ ID NO:7 and SEQ ID NO:8.

* * * * *